US012624067B2

(12) United States Patent
Minami

(10) Patent No.: US 12,624,067 B2
(45) Date of Patent: May 12, 2026

(54) CYCLIC PEPTIDE, CELL SCAFFOLD MATERIAL, CELL SEPARATING MATERIAL, AND MEDIUM

(71) Applicant: FUJIFILM Corporation, Tokyo (JP)

(72) Inventor: Koichi Minami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1058 days.

(21) Appl. No.: 17/643,527

(22) Filed: Dec. 9, 2021

(65) Prior Publication Data

US 2022/0098240 A1 Mar. 31, 2022

Related U.S. Application Data

(63) Continuation of application No. PCT/JP2020/022559, filed on Jun. 8, 2020.

(30) Foreign Application Priority Data

Jun. 11, 2019 (JP) ................................ 2019-108953

(51) Int. Cl.

| | |
|---|---|
| ***C07K 7/08*** | (2006.01) |
| ***C07K 7/06*** | (2006.01) |
| ***C12M 1/00*** | (2006.01) |
| ***C12M 1/12*** | (2006.01) |
| ***C12N 5/00*** | (2006.01) |

(52) U.S. Cl.

CPC .................. *C07K 7/08* (2013.01); *C07K 7/06* (2013.01); *C12M 25/14* (2013.01); *C12M 47/02* (2013.01); *C12N 5/0018* (2013.01)

(58) Field of Classification Search

None

See application file for complete search history.

(56) References Cited

U.S. PATENT DOCUMENTS

| | | | | |
|---|---|---|---|---|
| 5,493,007 | A | 2/1996 | Burnier et al. | |
| 6,664,367 | B1 * | 12/2003 | Rajagopalan | C07K 1/006 930/280 |
| 7,521,419 | B2 * | 4/2009 | Cuthbertson | A61K 47/60 514/21.1 |
| 2005/0070466 | A1 | 3/2005 | Cuthbertson et al. | |
| 2005/0164920 | A1 | 7/2005 | Doherty et al. | |
| 2018/0230184 | A1 | 8/2018 | Minami | |

FOREIGN PATENT DOCUMENTS

| | | | |
|---|---|---|---|
| JP | 6-509551 | A | 10/1994 |
| JP | 10-503205 | A | 3/1998 |
| JP | 2005-507376 | A | 3/2005 |
| JP | 2007-505145 | A | 3/2007 |
| JP | 2017-095443 | A | 6/2017 |
| WO | 03/006491 | A2 | 1/2003 |

OTHER PUBLICATIONS

He et al. Synthesis of cyclic prodrugs of RGD peptidomimetics with various macrocyclic ring sizes: evaluation of physiochemical, transport and antithrombotic properties. J. Peptide Res., 2003, 63, 331-342 (Year: 2003).*

Kelleman et al., "Incorporation of Thioether Building Blocks into an $\alpha_v\alpha_3$-Specific RGD Peptide: Synthesis and Biological Activity", Biopolymers (Peptide Science), vol. 71, pp. 686-695, 2003 (10 pages total).

Cao et al., "Evaluating the Effects of Charged Oligopeptide Motifs Coupled with RGD on Osteogenic Differentiation of Mesenchymal Stem Cells", ACS Appl. Mater. Interfaces, 2015, vol. 7, pp. 6698-6705 (8 pages total).

Extended European Search Report dated Jun. 9, 2022 from the European Patent Office in EP application No. 20823384.1.

(Continued)

*Primary Examiner* — Christina Bradley

(74) *Attorney, Agent, or Firm* — Sughrue Mion, PLLC

(57) ABSTRACT

There is provided a cyclic peptide having an amino acid sequence represented Formula (1). In the formula, $X^a$ and $X^b$, and $X^c$ and $X^d$ each independently represent amino acid residues crosslinked through a thioether bond; $X_1$ to $X_5$ each independently represent an amino acid residue; R represents an arginine residue; G represents a glycine residue; D represents an aspartic acid residue; and m1 to m5 each independently represent an integer of 0 or more. However, the total number of amino acid residues represented by $X^a$, $X^b$, $X^c$, and $X^d$ and represented by $X_1$, $X_3$, and $X_4$ is 7 to 16.

(1)

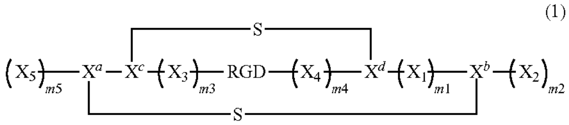

7 Claims, No Drawings

Specification includes a Sequence Listing.

(56) References Cited

OTHER PUBLICATIONS

Baker et al., "Cyclic RGD Peptide Analogues as Antiplatelet Antithrombotics", J. Mid. Chem., vol. 35, 1992, pp. 2040-2048 (10 pages total).
Office Action dated Sep. 27, 2022 from the Japanese Patent Office in JP Application No. 2021-526080.
Office Action issued Sep. 9, 2023 in Chinese Application No. 202080042692.X.
Chinese Office Action issued Feb. 9, 2024 in Application No. 202080042692.X.
International Search Report issued Jul. 28, 2020 in International Application No. PCT/JP2020/022559.
Written Opinion of the International Searching Authority issued Jul. 28, 2020 in International Application No. PCT/JP2020/022559.
International Preliminary Report on Patentability issued Dec. 14, 2021 in International Application No. PCT/JP2020/022559.
Barker et al., "Cyclic RGD Peptide Analogues as Antiplatelet Antithrombotics", J. Med. Chem., 1992, vol. 35, pp. 2040-2048 (9 pages total).
Ivanov et al., "Synthesis and Use of a New Bromoacetyl-Derivatized Heterotrifunctional Amino Acid for Conjugation of Cyclic RGD-Containing Peptides Derived from Human Bone Sialoprotein", Bioconjugate Chem., 1995, vol. 6, pp. 269-277 (9 pages total).

* cited by examiner

SEQUENCE LISTING

```
<160> NUMBER OF SEQ ID NOS: 52

<210> SEQ ID NO 1
<211> LENGTH: 11
<212> TYPE: PRT
```

-continued

<213> ORGANISM: Artificial Sequence
<220> FEATURE:
<223> OTHER INFORMATION: Synthetic Sequence, Integrin-binding Cyclic
      Peptide 1
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: 2-amino-3-(acetylamino)propanoic acid
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: Homocystein

<400> SEQUENCE: 1

Xaa Xaa Arg Gly Asp Xaa Phe Xaa Lys Lys Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 2
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: 2-amino-4-(acetylamino)butanoic acid
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: Homocystein

<400> SEQUENCE: 2

Xaa Xaa Arg Gly Asp Xaa Phe Xaa Lys Lys Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic -continued

```
      Peptide 3
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: N-delta-acetyl-ornithine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: Homocystein

<400> SEQUENCE: 3

Xaa Xaa Arg Gly Asp Xaa Phe Xaa Lys Lys Lys
1               5                   10


<210> SEQ ID NO 4
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 4
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: N-epsilon-acetyl-lysine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: Homocystein

<400> SEQUENCE: 4

Xaa Xaa Arg Gly Asp Xaa Phe Xaa Lys Lys Lys
1               5                   10


<210> SEQ ID NO 5
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 5
<220> FEATURE:
<221> NAME/KEY: THIOETH
```

<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: 2-amino-3-(acetylamino)propanoic acid
<220> FEATURE:
<221> NAME/KEY: MISC_FEATURE
<222> LOCATION: (8)..(8)
<223> OTHER INFORMATION: Homocystein

<400> SEQUENCE: 5

Xaa Xaa Arg Gly Asp Xaa Phe Xaa Lys Lys Lys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 6
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: 2-amino-3-(acetylamino)propanoic acid

<400> SEQUENCE: 6

Xaa Cys Arg Gly Asp Xaa Phe Cys Lys Lys Lys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 7
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: Homocystein
<220> FEATURE:

-continued

<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: 2-amino-4-(acetylamino)butanoic acid
<220> FEATURE:
<221> NAME/KEY: MISC_FEATURE
<222> LOCATION: (8)..(8)
<223> OTHER INFORMATION: Homocystein

<400> SEQUENCE: 7

Xaa Xaa Arg Gly Asp Xaa Phe Xaa Lys Lys Lys
1 5 10

<210> SEQ ID NO 8
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
Peptide 8
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: 2-amino-4-(acetylamino)butanoic acid

<400> SEQUENCE: 8

Xaa Cys Arg Gly Asp Xaa Phe Cys Lys Lys Lys
1 5 10

<210> SEQ ID NO 9
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
Peptide 9
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-delta-acetyl-ornithine
<220> FEATURE:
<221> NAME/KEY: MISC_FEATURE
<222> LOCATION: (8)..(8)
<223> OTHER INFORMATION: Homocystein

<400> SEQUENCE: 9

Xaa Xaa Arg Gly Asp Xaa Phe Xaa Lys Lys Lys
1 5 10

<210> SEQ ID NO 10
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 10
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-delta-acetyl-ornithine

<400> SEQUENCE: 10

Xaa Cys Arg Gly Asp Xaa Phe Cys Lys Lys Lys
1 5 10

<210> SEQ ID NO 11
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 11
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 11

Xaa Xaa Arg Gly Asp Xaa Phe Xaa Lys Lys Lys
1 5 10

<210> SEQ ID NO 12
<211> LENGTH: 11
<212> TYPE: PRT
<213> ORGANISM: Artificial Sequence -continued

```
<220> FEATURE:
<223> OTHER INFORMATION: Synthetic Sequence, Integrin-binding Cyclic
      Peptide 12
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-epsilon-acetyl-lysine

<400> SEQUENCE: 12

Xaa Cys Arg Gly Asp Xaa Phe Cys Lys Lys Lys
1               5                   10


<210> SEQ ID NO 13
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 13
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: 2-amino-3-(acetylamino)propanoic acid
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein

<400> SEQUENCE: 13

Xaa Xaa Arg Gly Asp Xaa Phe Cys Lys Lys Lys
1               5                   10


<210> SEQ ID NO 14
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 14
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: 2-amino-3-(acetylamino)propanoic acid
```

<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (8)..(8)
<223> OTHER INFORMATION: Homocystein

<400> SEQUENCE: 14

Xaa Xaa Arg Gly Asp Cys Phe Xaa Lys Lys Lys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 15
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: N-delta-acetyl-ornithine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein

<400> SEQUENCE: 15

Xaa Xaa Arg Gly Asp Xaa Phe Cys Lys Lys Lys
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 16
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: N-delta-acetyl-ornithine
<220> FEATURE:
<221> NAME/KEY: MISC_FEATURE
<222> LOCATION: (8)..(8)
<223> OTHER INFORMATION: Homocystein

<400> SEQUENCE: 16

-continued

```
Xaa Xaa Arg Gly Asp Cys Phe Xaa Lys Lys Lys
1               5                   10


<210> SEQ ID NO 17
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 17
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-epsilon-acetyl-lysine

<400> SEQUENCE: 17

Xaa Xaa Arg Gly Asp Xaa Phe Cys Lys Lys Lys
1               5                   10


<210> SEQ ID NO 18
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 18
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 18

Xaa Cys Arg Gly Asp Xaa Phe Xaa Lys Lys Lys
1               5                   10


<210> SEQ ID NO 19
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 19
```

-continued

<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: 2-amino-4-(acetylamino)butanoic acid

<400> SEQUENCE: 19

```
Xaa Xaa Arg Gly Asp Xaa Phe Cys Lys Lys Lys
1               5                   10
```

<210> SEQ ID NO 20
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 20
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: 2-amino-4-(acetylamino)butanoic acid
<220> FEATURE:
<221> NAME/KEY: MISC_FEATURE
<222> LOCATION: (8)..(8)
<223> OTHER INFORMATION: Homocystein

<400> SEQUENCE: 20

```
Xaa Cys Arg Gly Asp Xaa Phe Xaa Lys Lys Lys
1               5                   10
```

<210> SEQ ID NO 21
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 21
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N-epsilon-acetyl-lysine
<220> FEATURE:
<221> NAME/KEY: MISC_FEATURE
<222> LOCATION: (2)..(2)

<223> OTHER INFORMATION: 2-amino-3-(acetylamino)propanoic acid
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: Homocystein

<400> SEQUENCE: 21

Xaa Xaa Arg Gly Asp Xaa Phe Xaa Lys Lys Lys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic Sequence, Integrin-binding Cyclic
      Peptide 22
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 22

Xaa Xaa Arg Gly Asp Xaa Phe Xaa Lys
1               5

<210> SEQ ID NO 23
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 23
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N-Acetyl-L-isoleucine
<220> FEATURE:
<221> NAME/KEY: MISC_FEATURE
<222> LOCATION: (2)..(2)
<223> OTHER INFORMATION: N-delta-acetyl-ornithine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: penicillamine

<400> SEQUENCE: 23

```
Xaa Xaa Arg Gly Asp Xaa Phe Xaa Lys Lys Lys
1               5                   10
```

<210> SEQ ID NO 24
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
Peptide 24
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N-Acetyl-L-Glutamic acid
<220> FEATURE:
<221> NAME/KEY: MISC_FEATURE
<222> LOCATION: (2)..(2)
<223> OTHER INFORMATION: N-delta-acetyl-ornithine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: penicillamine

<400> SEQUENCE: 24

```
Xaa Xaa Arg Gly Asp Xaa Phe Xaa Lys Lys Lys
1               5                   10
```

<210> SEQ ID NO 25
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
Peptide 25
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- tyrosine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:

<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 25

Xaa Xaa Arg Gly Asp Xaa Phe Xaa Lys Lys Lys
1 5 10

<210> SEQ ID NO 26
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 26
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N-alpha-acetyl-leucine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 26

Xaa Xaa Arg Gly Asp Xaa Phe Xaa Lys Lys Lys
1 5 10

<210> SEQ ID NO 27
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 27
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- threonine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 27

Xaa Xaa Arg Gly Asp Xaa Phe Xaa Lys Lys Lys
1 5 10

<210> SEQ ID NO 28
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 28
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- valine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 28

Xaa Xaa Arg Gly Asp Xaa Phe Xaa Lys Lys Lys
1 5 10

<210> SEQ ID NO 29
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 29
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- aspartic acid
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)

<223> OTHER INFORMATION: Homocystein

<400> SEQUENCE: 29

Xaa Xaa Arg Gly Asp Xaa Phe Xaa Lys Lys Lys
1 5 10

<210> SEQ ID NO 30
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 30
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- glutamic acid
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 30

Xaa Xaa Arg Gly Asp Xaa Phe Xaa Lys Lys Lys
1 5 10

<210> SEQ ID NO 31
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 31
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleusine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 31

Xaa Xaa Arg Gly Asp Xaa Pro Xaa Lys Lys Lys
1 5 10

<210> SEQ ID NO 32
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 32
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleusine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 32

Xaa Xaa Arg Gly Asp Xaa Tyr Xaa Lys Lys Lys
1 5 10

<210> SEQ ID NO 33
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic Peptide 33
<220> FEATURE:
<221> NAME/KEY: THIOETH
<222> LOCATION: (1)..(9)
<223> OTHER INFORMATION: Thioether bridge between residues 1 and 9
<220> FEATURE:
<221> NAME/KEY: MISC_FEATURE
<222> LOCATION: (1)..(1)
<223> OTHER INFORMATION: N- alpha-acetyl- isoleusine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (9)..(9)
<223> OTHER INFORMATION: Homocystein

<400> SEQUENCE: 33

Xaa Xaa Arg Gly Asp Xaa Phe Arg Xaa Lys Lys Lys
1 5 10

<210> SEQ ID NO 34
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
      Peptide 34
<220> FEATURE:
<221> NAME/KEY: THIOETH
<222> LOCATION: (1)..(9)
<223> OTHER INFORMATION: Thioether bridge between residues 1 and 9
<220> FEATURE:
<221> NAME/KEY: MISC_FEATURE
<222> LOCATION: (1)..(1)
<223> OTHER INFORMATION: N- alpha-acetyl- isoleusine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (9)..(9)
<223> OTHER INFORMATION: Homocystein

<400> SEQUENCE: 34

Xaa Xaa Arg Gly Asp Xaa Phe Ala Xaa Lys Lys Lys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
      Peptide 35
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- isoleusine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 35

Xaa Xaa Arg Gly Asp Xaa Phe Xaa Ala Lys Lys Lys
1               5                   10

<210> SEQ ID NO 36

<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
Peptide 36
<220> FEATURE:
<221> NAME/KEY: THIOETH
<222> LOCATION: (2)..(9)
<223> OTHER INFORMATION: Thioether bridge between residues 2 and 9
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (3)..(7)
<223> OTHER INFORMATION: Thioether bridge between residues 3 and 7
<220> FEATURE:
<221> NAME/KEY: MISC_FEATURE
<222> LOCATION: (3)..(3)
<223> OTHER INFORMATION: Homocystein
<220> FEATURE:
<221> NAME/KEY: MISC_FEATURE
<222> LOCATION: (7)..(7)
<223> OTHER INFORMATION: N-epsilon-acetyl-lysine
<220> FEATURE:
<221> NAME/KEY: MISC_FEATURE
<222> LOCATION: (9)..(9)
<223> OTHER INFORMATION: N-epsilon-acetyl-lysine

<400> SEQUENCE: 36

Ala Xaa Xaa Arg Gly Asp Xaa Phe Xaa Lys Lys Lys
1 5 10

<210> SEQ ID NO 37
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
Peptide 37
<220> FEATURE:
<221> NAME/KEY: THIOETH
<222> LOCATION: (4)..(11)
<223> OTHER INFORMATION: Thioether bridge between residues 4 and 11
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (5)..(9)
<223> OTHER INFORMATION: Thioether bridge between residues 5 and 9
<220> FEATURE:
<221> NAME/KEY: MISC_FEATURE
<222> LOCATION: (5)..(5)
<223> OTHER INFORMATION: Homocystein
<220> FEATURE:
<221> NAME/KEY: MISC_FEATURE
<222> LOCATION: (9)..(9)
<223> OTHER INFORMATION: N-epsilon-acetyl-lysine
<220> FEATURE:
<221> NAME/KEY: MISC_FEATURE
<222> LOCATION: (11)..(11)
<223> OTHER INFORMATION: N-epsilon-acetyl-lysine

<400> SEQUENCE: 37

Lys Lys Lys Xaa Xaa Arg Gly Asp Xaa Phe Xaa Ala
1 5 10

<210> SEQ ID NO 38
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
Peptide 38
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- valine
<220> FEATURE:
<221> NAME/KEY: MISC_FEATURE
<222> LOCATION: (2)..(2)
<223> OTHER INFORMATION: N-delta-acetyl-ornithine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: Homocystein

<400> SEQUENCE: 38

Xaa Xaa Arg Gly Asp Xaa Phe Xaa Lys Lys Lys
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
Peptide 39
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- aspartic acid
<220> FEATURE:
<221> NAME/KEY: MISC_FEATURE
<222> LOCATION: (2)..(2)
<223> OTHER INFORMATION: N-delta-acetyl-ornithine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: Homocystein

<400> SEQUENCE: 39

Xaa Xaa Arg Gly Asp Xaa Phe Xaa Lys Lys Lys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
Peptide 40

<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- glutamic acid
<220> FEATURE:
<221> NAME/KEY: MISC_FEATURE
<222> LOCATION: (2)..(2)
<223> OTHER INFORMATION: N-delta-acetyl-ornithine
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: Homocystein
<220> FEATURE:
<221> NAME/KEY: MISC_FEATURE
<222> LOCATION: (8)..(8)
<223> OTHER INFORMATION: Homocystein

<400> SEQUENCE: 40

Xaa Xaa Arg Gly Asp Xaa Phe Xaa Lys Lys Lys
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 41
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- valine
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-delta-acetyl-ornithine
<220> FEATURE:
<221> NAME/KEY: MISC_FEATURE
<222> LOCATION: (8)..(8)
<223> OTHER INFORMATION: Homocystein

<400> SEQUENCE: 41

Xaa Xaa Arg Gly Asp Xaa Phe Xaa Lys Lys Lys
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 42
<220> FEATURE:
<221> NAME/KEY: THIOETH
<222> LOCATION: (1)..(8)

<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- aspartic acid
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-delta-acetyl-ornithine
<220> FEATURE:
<221> NAME/KEY: MISC_FEATURE
<222> LOCATION: (8)..(8)
<223> OTHER INFORMATION: Homocystein

<400> SEQUENCE: 42

```
Xaa Xaa Arg Gly Asp Xaa Phe Xaa Lys Lys Lys
1               5                   10
```

<210> SEQ ID NO 43
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic
      Peptide 43
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- glutamic acid
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-delta-acetyl-ornithine
<220> FEATURE:
<221> NAME/KEY: MISC_FEATURE
<222> LOCATION: (8)..(8)
<223> OTHER INFORMATION: Homocystein

<400> SEQUENCE: 43

```
Xaa Xaa Arg Gly Asp Xaa Phe Xaa Lys Lys Lys
1               5                   10
```

<210> SEQ ID NO 44
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
      Peptide 44
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- valine
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 44

Xaa Xaa Arg Gly Asp Xaa Phe Xaa Ala Lys Lys Lys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
      Peptide 45
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- aspartic acid
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 45

Xaa Xaa Arg Gly Asp Xaa Phe Xaa Ala Lys Lys Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
      Peptide 46
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- glutamic acid
<220> FEATURE:

-continued

<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-epsilon-acetyl-lysine
<220> FEATURE:
<221> NAME/KEY: MISC_FEATURE
<222> LOCATION: (8)..(8)
<223> OTHER INFORMATION: Homocystein

<400> SEQUENCE: 46

Xaa Xaa Arg Gly Asp Xaa Phe Xaa Ala Lys Lys Lys
1 5 10

<210> SEQ ID NO 47
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic Peptide 47
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N- alpha-acetyl- glutamic acid
<220> FEATURE:
<221> NAME/KEY: MISC_FEATURE
<222> LOCATION: (2)..(2)
<223> OTHER INFORMATION: Homocystein
<220> FEATURE:
<221> NAME/KEY: THIOETH
<222> LOCATION: (2)..(6)
<223> OTHER INFORMATION: Thioether bridge between residues 2 and 6
<220> FEATURE:
<221> NAME/KEY: MISC_FEATURE
<222> LOCATION: (6)..(6)
<223> OTHER INFORMATION: N-delta-acetyl-ornithine
<220> FEATURE:
<221> NAME/KEY: MISC_FEATURE
<222> LOCATION: (8)..(8)
<223> OTHER INFORMATION: Homocystein

<400> SEQUENCE: 47

Xaa Xaa Arg Gly Asp Xaa Phe Xaa Ala Lys Lys Lys
1 5 10

<210> SEQ ID NO 48
<211> LENGTH: 11
<212> TYPE: PRT
<213> ORGANISM: Artificial Sequence
<220> FEATURE:
<223> OTHER INFORMATION: Synthetic Sequence, Integrin-binding Cyclic Peptide 48
<220> FEATURE:
<221> NAME/KEY: THIOETH
<222> LOCATION: (1)..(8)
<223> OTHER INFORMATION: Thioether bridge between residues 1 and 8
<220> FEATURE:
<221> NAME/KEY: MISC_FEATURE
<222> LOCATION: (1)..(1)
<223> OTHER INFORMATION: N-epsilon-acetyl-lysine
<220> FEATURE:
<221> NAME/KEY: DISULFID
<222> LOCATION: (2)..(6)
<223> OTHER INFORMATION: Disulfid bridge between residues 2 and 6

<400> SEQUENCE: 48

Xaa Cys Arg Gly Asp Cys Phe Cys Lys Lys Lys
1 5 10

<210> SEQ ID NO 49
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 49
<220> FEATURE:
<221> NAME/KEY: DISULFID
<222> LOCATION: (2)..(10)
<223> OTHER INFORMATION: Disulfid bridge between residues 2 and 10
<220> FEATURE:
<221> NAME/KEY: DISULFID
<222> LOCATION: (4)..(8)
<223> OTHER INFORMATION: Disulfid bridge between residues 4 and 8

<400> SEQUENCE: 49

Ala Cys Asp Cys Arg Gly Asp Cys Phe Cys Gly Lys Lys Lys
1 5 10

<210> SEQ ID NO 50
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 50

Ala Lys Lys Lys
1

<210> SEQ ID NO 51
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 51

Ala Tyr His Arg Gly Glu Leu Val Trp Glu
1 5 10

<210> SEQ ID NO 52
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 52

Ser Ala Trp His Gly Glu Leu Val Trp
1 5

CYCLIC PEPTIDE, CELL SCAFFOLD MATERIAL, CELL SEPARATING MATERIAL, AND MEDIUM

CROSS-REFERENCE TO RELATED APPLICATION

This application is a Continuation of International Application No. PCT/JP2020/022559, filed Jun. 8, 2020, which claims priority to Japanese Patent Application No. 2019-108953 filed Jun. 11, 2019. Each of the above applications is hereby expressly incorporated by reference, in its entirety, into the present application.

INCORPORATION BY REFERENCE OF SEQUENCE LISTING

The content of the electronically submitted sequence listing, file name: Q268729SubstituteSequenceListing.txt; size: 35,120 bytes; and date of creation: Jan. 14, 2026, is hereby incorporated by reference in their entirety.

BACKGROUND OF THE INVENTION

1. Field of the Invention

The present disclosure relates to a cyclic peptide, a cell scaffold material, a cell separating material, and a medium.

2. Description of the Related Art

Integrin is a cell adhesion molecule and is a heterodimeric protein consisting of two subunits, an α chain and a β chain. Integrin plays an important role not only in cell adhesion but also in cel extension, cell migration, cell proliferation, tissue formation, cancer metastasis, tissue repair, blood coagulation, and the like.

In the related art, cyclic peptides such as those described in JP2005-507376A, JP1994-509551A (JP-H6-509551A), and Bioconjugate Chem., 1995, 6, p. 269-277, are known. JP2005-507376A discloses a cyclic peptide that is cyclized by a disulfide bond and that binds to integrin. Other cyclic peptides having an affinity to integrin are also known. For example, JP1994-509551A (JP-H6-509551A) discloses a cyclic peptide obtained by cyclizing Tyr-Arg-Gly-Asp, as a platelet aggregation inhibitor having high specificity to GP $II_b$ $III_a$. In addition, Bioconjugate Chem., 1995, 6, p. 269-277 describes a technique for subjecting a peptide to cyclization and/or binding to a carrier protein or glass coverslip using (bromoacetyl) diaminopropionic acid.

SUMMARY OF THE INVENTION

An object to be achieved by an aspect of the present disclosure is to provide a cyclic peptide excellent in the integrin binding property and excellent in the molecule stability, for example, excellent in the alkali resistance, and a cell scaffold material, a cell separating material, and a medium, which contain the cyclic peptide.

The technique for achieving the above object includes the following aspects.

<1> A cyclic peptide comprising an amino acid sequence represented Formula (1).

(1)

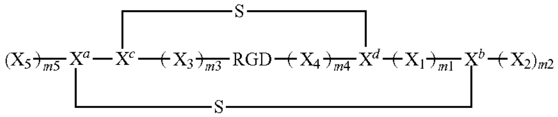

In Formula (1), $X^a$ and $X^b$, and $X^c$ and $X^d$ each independently represent amino acid residues crosslinked through a thioether bond, $X_1$ to $X_5$ independently represent an amino acid residue, R represents an arginine residue; G represents a glycine residue; D represents an aspartic acid residue, and m1 to m5 each independently represent an integer of 0 or more, provided that a total number of amino acid residues represented by $X^a$, $X^b$, $X^c$, and $X^d$, amino acid residues represented by $X_1$, $X_3$, and $X_4$, and amino acid residues of RGD is 7 to 16.

<2> The cyclic peptide according to <1>, in which $X_2$ and $X_5$ in Formula (1) comprise an amino acid residue derived from an amino acid having an immobilizing functional group in a side chain.

<3> The cyclic peptide according to <2>, in which the immobilizing functional group is an amino group or a thiol group.

<4> The cyclic peptide according to <2> or <3>, in which the amino acid having the immobilizing functional group in the side chain is at least one amino acid selected from the group consisting of L-lysine, D-lysine, L-cysteine, D-cysteine, L-homocysteine, and D-homocysteine.

<5> The cyclic peptide according to any one of <1> to <4>, in which any one of $X^c$ or $X^d$ in Formula (1) is an amino acid residue, which is derived from an amino acid selected from the group consisting of (2S)-2-amino-3-[(2-acetyl)amino]propanoic acid, (2R)-2-amino-3-[(2-acetyl)amino]propanoic acid, (2S)-2-amino-4-[(2-acetyl)amino]butanoic acid, (2R)-2-amino-4-[(2-acetyl)amino]butanoic acid, N-δ-acetyl-L-ornithine, N-δ-acetyl-D-ornithine, N-ε-acetyl-L-lysine, and N-ε-acetyl-D-lysine, and the other is an amino acid residue derived from L-homocysteine, D-homocysteine, L-penicillamine, or D-penicillamine.

<6> The cyclic peptide according to any one of <1> to <5>, in which $X^b$ in Formula (1) is an amino acid residue derived from L-homocysteine, D-homocysteine, L-penicillamine, or D-penicillamine.

<7> The cyclic peptide according to any one of <1> to <6>, in which the amino acid sequence represented by Formula (1) is an amino acid sequence represented Formula (2).

(2)

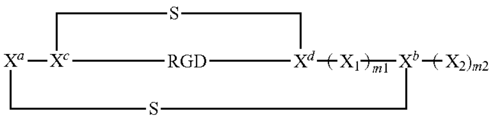

In Formula (2), $X^a$ and $X^b$, and $X^c$ and $X^d$ each independently represent amino acid residues crosslinked through a thioether bond; $X_1$ and $X_2$ each independently represent an amino acid residue; R represents an arginine residue; G represents a glycine residue; D represents an aspartic acid residue; and m1 and m2 each independently represent an integer of 1 or more. However, a total number of amino acid residues represented by $X^a$, $X^b$, $X^c$, and $X^d$, amino acid residues represented by $X_1$, and amino acid residues of RGD is 7 to 14.

<8> The cyclic peptide according to <7>, in which any one of $X^c$ or $X^d$ in Formula (2) is an amino acid residue derived from an amino acid having an acetyl group in a side chain, which is selected from the group consisting of (2S)-2-amino-3-[(2-acetyl)amino]propanoic acid, (2R)-2-amino-3-[(2-acetyl)amino]propanoic acid, (2S)-2-amino-4-[(2-acetyl)amino]butanoic acid, (2R)-2-amino-4-[(2-acetyl) amino]butanoic acid, N-δ-acetyl-L-ornithine, N-δ-acetyl-D-ornithine, N-ε-acetyl-L-lysine, and N-ε-acetyl-D-lysine, and the other is an amino acid residue derived from L-homocysteine, D-homocysteine, L-penicillamine, or D-penicillamine.

<9> The cyclic peptide according to <7> or <8>, in which $X^b$ in Formula (2) is an amino acid residue derived from L-homocysteine, D-homocysteine, L-penicillamine, or D-penicillamine.

<10> The cyclic peptide according to any one of <7> to <9>, in which $X^a$ in Formula (2) is an amino acid residue represented by the following Structural Formula (r).

(r)

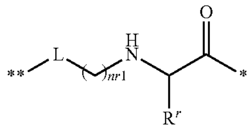

In the structural formula (r), $R^r$ represents a hydrogen atom or a monovalent organic group; L represents a divalent linking group represented by $-(CH_2)_{L1}-C(=O)-$ or $-(CH_2)_{L1}-C(=O)-NH-$, where L1 represents an integer of 0 or more and 10 or less; nr1 represents an integer of 0 or more; * represents a bonding site to an adjacent amino acid residue; and ** represents a bonding site to a sulfur atom in the thioether bond.

<11> The cyclic peptide according to any one of <7> to <10>, in which $X^b$ in Formula (2) is an amino acid residue derived from L-homocysteine, D-homocysteine, L-penicillamine, or D-penicillamine, and $X^a$ is an amino acid residue derived from an amino acid selected from the group consisting of (2S)-2-amino-3-[(2-acetyl)amino]propanoic acid, (2R)-2-amino-3-[(2-acetyl)amino]propanoic acid, (2S)-2-amino-4-[(2-acetyl)amino]butanoic acid, (2R)-2-amino-4-[(2-acetyl)amino]butanoic acid, N-δ-acetyl-L-ornithine, N-δ-acetyl-D-ornithine, N-ε-acetyl-L-lysine, N-ε-acetyl-D-lysine, and (2S,3S)-2-[(acetyl)amino]-3-methyl-pentanoic acid.

<12> The cyclic peptide according to any one of <1> to <11>, in which $X^a$ is an amino acid residue derived from any amino acid in which an acetyl group is bonded to an α carbon; $X^b$ is an amino acid residue derived from homocysteine; $X^c$ is an amino acid residue derived from homocysteine; $X^d$ is an amino acid residue derived from N-δ-acetyl-ornithine or an amino acid residue derived from N-ε-acetyl-lysine; and $(X_1)_{m1}$ is F as a whole, or $X^a$ is an amino acid residue derived from any amino acid in which an acetyl group is bonded to an α carbon; $X^b$ is an amino acid residue derived from homocysteine; $X^c$ is an amino acid residue derived from N-δ-acetyl-ornithine or an amino acid residue derived from N-ε-acetyl-lysine; $X^d$ is an amino acid residue derived from homocysteine; and $(X_1)_{m1}$ is F as a whole.

<13> A cell scaffold material comprising the cyclic peptide according to any one of <1> to <12> and a base material.

<14> A cell separating material comprising the cyclic peptide according to any one of <1> to <12> and a holding material.

<15> A medium comprising the cyclic peptide according to any one of <1> to <12> and a culture component.

According to an aspect of the present invention, there is provided a cyclic peptide excellent in the integrin binding property and excellent in the molecule stability, for example, excellent in the alkali resistance, and a cell scaffold material, a cell separating material, and a medium, which contain the cyclic peptide.

DESCRIPTION OF THE PREFERRED EMBODIMENTS

Hereinafter, the contents of the present disclosure will be described in detail. The description of the configuration requirements described below is based on the representative embodiments of the present disclosure; however, the present disclosure is not limited to such embodiments.

A range of numerical values shown using "to" in the disclosure means a range including numerical values before and after "to" as a minimum value and a maximum value.

In the range of numerical values disclosed stepwise in the present disclosure, an upper limit value and a lower limit value disclosed in a certain range of numerical values may be replaced with an upper limit value and a lower limit value disclosed in another range of numerical values disclosed in stepwise. In addition, in the range of numerical values disclosed in the present disclosure, an upper limit value and a lower limit value disclosed in a certain range of numerical values may be replaced with values shown in examples.

In the present disclosure, a combination of two or more preferred aspects is a more preferred aspect.

In the present disclosure, in a case where a plurality of substances corresponding to each component are present, unless otherwise particularly specified, the amount of each of components means the total amount of the plurality of substances.

In the present disclosure, the term "process" includes not only an independent process but also a process that cannot be clearly distinguished from other processes, as long as the intended purpose of the process is achieved.

(Cyclic Peptide)

The cyclic peptide according to the present disclosure has an amino acid sequence (hereinafter, also referred to as a "specific amino acid sequence") represented Formula (1).

(1)

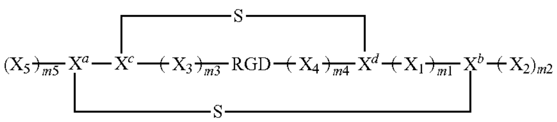

In Formula (1), $X^a$ and $X^b$, and $X^c$ and $X^d$ each independently represent amino acid residues bonded through a thioether bond; $X_1$ to $X_5$ each independently represent an amino acid residue; R represents an arginine residue; G represents a glycine residue; D represents an aspartic acid residue; and m1 to m5 each independently represent an integer of 0 or more. However, the total number of amino acid residues represented by $X^a$, $X^b$, $X^c$, and $X^d$ and represented by $X_1$, $X_3$, and $X_4$ is 7 to 16.

A cyclic peptide (hereinafter, also referred to as "an integrin-binding cyclic peptide") having an integrin binding property has an ability to bind to integrin on the cell surface of the cellular plasma membrane. Integrin is one of the cell adhesion molecules. Since an integrin-binding cyclic peptide bind to the integrin on the cell surface, it is possible to use the integrin-binding cyclic peptide in a scaffolding material for cell culture, a cell separating material for cell separation, various cell culture media, and the like, and thus is a useful molecule. However, while a cyclic peptide may have a high binding property and a high specificity with respect to a cell adhesion molecule such as integrin as compared with a linear peptide, the molecule stability of the cyclic peptide tends to be low as compared with the linear peptide.

In addition, a cyclic peptide tends to have low alkali resistance; low acid resistance; and low resistance to actinic rays such as an X ray and a γ ray. The integrin-binding cyclic peptide is also degraded during long-term use or repeated use due to low molecule stability thereof, and thus the desired effect could not be obtained for a long period of time. Furthermore, a cyclic peptide does not always have a higher binding property than a linear peptide, and the integrin binding property changes depending on the amino acid sequence included in the cyclic peptide. As a result, regarding the cyclic peptide, it has not been easy to obtain an integrin-binding cyclic peptide in which both the molecule stability and the integrin binding property are excellent.

As a result of diligent studies, the inventor has found that a cyclic peptide having a specific amino acid sequence and a specific structure is excellent in both molecule stability and integrin binding property. Although the reason therefor is not clear, it is presumed as follows.

Since the cyclic peptide having a specific structure according to the present disclosure contains two cyclic moieties (hereinafter, also may be referred to as "cyclic segments") in which amino acid residues are crosslinked by a thioether bond at a specific moiety in the amino acid sequence, and since the total number of amino acid residues represented by $X^a$, $X^b$, $X^c$, and $X^d$ and represented by $X_1$, $X_3$, and $X_4$, and RGD is 7 to 14, an RGD sequence is retained by two cyclic moieties, that is, the RGD sequence is retained by the two cyclic moieties in a nested manner. In addition, it is presumed as follows. Since the disulfide bond contained in the cyclic peptide described in JP2005-507376A is a quasi covalent bond, this disulfide bond is easily cleaved by a reducing agent or the like contained in a medium or the like, and thus sufficient molecule stability can be obtained. In contrast, since the thioether bond which is a covalent bond is more stable than the disulfide bond, the cyclic peptide according to the present disclosure is, for example, excellent in molecule stability in terms of alkali resistance and also excellent in integrin binding property.

Hereinafter, the details of the cyclic peptide according to the present disclosure will be described.

<Amino Acid and Amino Acid Residue>

In the present disclosure, an amino acid is represented by, in principle, using the name, the abbreviation, and the like adopted by INTERNATIONAL UNION OF PURE AND APPLIED CHEMISTRY and INTERNATIONAL UNION OF BIOCHEMISTRY AND MOLECULAR BIOLOGY IUPAC-IUB Joint Commission on Chemical Nomenclature (JCBN).

In addition, an amino acid residue is represented by using an abbreviation of an amino acid from which the amino acid residue is derived.

In the present disclosure, unless otherwise specified, an amino acid sequence (also referred to as a "primary structure") of a peptide or protein is represented so that amino acid residues are aligned in a row from the N-terminal to the C-terminal from the left end to the right end. In a case where an amino acid residue in the amino acid sequence of a peptide or protein, including the position thereof, is specified, it may be represented by adding a number indicating the number of the amino acid residue from the N-terminal side to the right side of the abbreviation of the amino acid residue. For example, the lysine at the second position from the N-terminal may be represented as Lys2.

In addition, in a case where an amino acid is represented using the name thereof, and isomers having an enantiomeric relationship, that is, an L-form and a D-form are present, the amino acid may be, in principle, the L-form or the D-form except for the case where the distinction between the L-form and the D-form is explicitly shown. For example, "isoleucine" represents "L-isoleucine" or "D-isoleucine", and the same applies to the amino acid residue. Similarly, also in a case where an amino acid is represented using the abbreviation (the three letter abbreviation or the one letter abbreviation) thereof, and isomers having an enantiomeric relationship, that is, an L-form and a D-form are present, the amino acid may be, in principle, the L-form or the D-form except for the case where the distinction between the L-form and the D-form is explicitly shown. For example, "Lys" represents both "L-lysine" and "D-lysine", and the same applies to the amino acid residue. In addition, the L-form and the D-form can be each independently selected for each amino acid and each amino acid residue. However, in the RGD sequence present in the cyclic segment, all amino acid residues have an L-form. Except for the above RGD sequence, all the amino acid residues present in the cyclic peptide may be amino acid residues having an L-form or may be amino acid residues having a D-form, or both amino acid residues having an L-form and amino acid residues having a D-form may be present.

In addition, in a case where an amino acid is represented by a name thereof, and an isomer having a diastereomeric relationship is present, the isomer is not included in the amino acid specified by the name. The prefix "allo" is used to treat a diastereomer as a different kind of amino acid. For example, "threonine" does not include "allothreonine". The same applies to the amino acid residue.

Table 1 shows names and abbreviations (one letter abbreviations and three letter abbreviations) of amino acids for which one letter abbreviations and three letter abbreviations are officially approved.

TABLE 1

| One letter abbreviation | Three letter abbreviation | Name |
|---|---|---|
| A | Ala | Alanine |
| B | Asx | Aspartic acid or asparagine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |

TABLE 1-continued

| One letter abbreviation | Three letter abbreviation | Name |
|---|---|---|
| M | Met | Methionine |
| N | Asn | Asparagine |
| O | Pyl | Pyrrolysine |
| P | Pro | Proline |
| Q | Gln | Glutamine |
| R | Arg | Arginine |
| S | Ser | Serine |
| T | Thr | Threonine |
| U | Sec | Selenocysteine |
| V | Val | Valine |
| W | Trp | Tryptophan |
| X | Xaa | Any amino acid |
| Y | Tyr | Tyrosine |
| Z | Glx | Glutamic acid or glutamine |

The amino acid residues contained in the cyclic peptide according to the present disclosure are not limited to the amino acid residues derived from the amino acids listed in Table 1 above and may be amino acid residues derived from unusual amino acids. Examples of the unusual amino acids are listed in Table 2 below; however, the unusual amino acids are not limited thereto.

TABLE 2

| Three letter abbreviation | Name |
|---|---|
| Aad | Homoglutamic acid |
| βAad | 3-aminoadipic acid |
| Abu | 2-aminobutanoic acid |
| $A_2$bu | 2,4-diaminobutanoic acid |
| Ahx | 2-aminohexanoic acid |
| Ahe | 2-aminoheptanoic acid |
| Aib | 2-aminoisobutyric acid |
| εAhx | 6-aminohexanoic acid |
| βAla | β-alanine |
| Ape | 2-aminopentanoic acid |
| $A_2$pr | 2,3-diaminopropanoic acid |
| Apm | 2-aminopimelic acid |
| $A_2$pm | 2,6-diaminopimelic acid |
| Cit | Citrulline |
| Cya | Cysteic acid |
| Dbu | 2,4-diaminobutanoic acid |
| Dpm | 2,6-diaminopimelic acid |
| Pen | Penicillamine |
| Dpr | 2,3-diaminopropanoic acid |
| Gla | 4-carboxyglutamic acid |
| Glp | 5-oxoproline |
| Hcy | Homocysteine |
| Hly | Homolysine |
| Hse | Homoserine |
| Hsl | Homoserine lactone |
| 5Hyl | 5-hydroxylysine (Hyl) |
| aHyl | Allohydoxylysine |
| 3Hyp | 3-hydroxyproline |
| 4Hyp | 4-hydroxyproline |
| aIle | Alloisoleucine |
| Nle | Norleucine |
| Nva | Norvaline |
| Orn | Ornithine |
| Sar | Sarcosine |
| aThr | Allothreonine |
| Thx | Thyroxine |

Any amino acid residue contained in the cyclic peptide according to the present disclosure may be chemically modified. The chemical modification of the amino acid residue is not particularly limited as long as it is a chemical modification usually carried out on the amino acid residue. Examples of the chemical modification of an amino acid residue include N-acetylation, N-formylation, or N-acylation, or polyethylene glycol modification (PEGylation) of an amino group present in the amino acid residue and amidation, PEGylation, or the like of a carboxy group present in the amino acid residue.

In the specific amino acid sequence, in a case where $X_5$ or $X^a$ in Formula (1) is the N-terminal amino group of the cyclic peptide, the N-terminal amino group residue is not particularly limited, and may be subjected to N-terminal modification such as N-acetylation, N-formylation, N-acylation, or PEGylation, or may be the amino group as it is.

In addition, in the specific amino acid sequence, in a case where $X_2$ and $X^b$ in Formula (1) are the C-terminal carboxy group of the cyclic peptide, the C-terminal carboxy group is not particularly limited, and may be subjected to C-terminal modification such as amidation or PEGylation or may the carboxy group as it is.

The cyclic peptide according to the present disclosure has a specific amino acid sequence, where $X^a$ and $X^b$, and $X^c$ and $X^d$ each independently present amino acid residues bonded through a thioether bond, and $X_1$ to $X_5$ each independently represent an amino acid residue.

<<Amino Acid Residues $X^a$ to $X^d$>>

The cyclic peptide according to the present disclosure has a specific amino acid sequence, where $X^c$ and $X^d$, and $X^a$ and $X^b$ each independently present amino acid residues bonded through a thioether bond.

In addition, "—S—" in Formula (1) represents that $X^c$ and $X^d$, and $X^a$ and $X^b$ are respectively crosslinked through a thioether bond.

It is presumed that, in the specific amino acid sequence contained in the cyclic peptide according to the present disclosure, the molecule stability is excellent as compared with the cyclic peptide having amino acid residues crosslinked by a disulfide bond since the amino acid residue $X_c$ and the amino acid residue $X^d$, and the amino acid residue $X^a$ and the amino acid residue $X^b$ described later are each crosslinked by a thioether bond and thus there is structural irreversibility as compared with a disulfide bond, the details of which are not clear.

The amino acid before the formation of a thioether bond is not particularly limited; however, examples thereof include a combination in which any one of $X_c$ or $X_d$ is an amino acid residue derived from an amino acid having a thiol group, and the other is an amino acid residue derived from an amino acid protected by an organic group having a halogen atom.

Similarly, the amino acid before the formation of a thioether bond is not particularly limited; however, examples thereof include a combination in which any one of $X^a$ and $X^b$ is an amino acid residue derived from an amino acid having a thiol group, and the other is an amino acid residue derived from an amino acid protected by an organic group having a halogen atom.

Suitable examples of the organic group having a halogen atom include a haloacetyl group.

In the present disclosure, the "main chain" in a cyclic peptide refers to a peptide chain that is relatively longest and is a stem among the chain moieties in the cyclic peptide. The "side chain" means a chain that is bonded to the main chain of a cyclic peptide.

The main chain in an amino acid or amino acid residue corresponds to the "main chain" in a cyclic peptide, and the side chain in an amino acid or amino acid residue is a side chain that is bonded to the main chain of a cyclic peptide.

Hereinafter, an amino acid residue derived from an amino acid having a thiol group that can be taken by $X^a$ to $X^d$ before the formation of a thioether bond will be described.

[Amino Acid Residue Derived from Amino Acid Having Thiol Group]

The amino acid having a thiol group is preferably an amino acid having a thiol group on the side chain from the viewpoint of reactivity. It is preferable that the main chain of an amino acid does not contain a thiol group.

The amino acid residue having a thiol group on the side chain is not particularly limited; however, suitable examples thereof include an amino acid residue represented by the following structure (t-1) or (t-2).

(t-1)

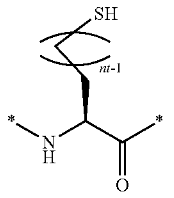

(t-2)

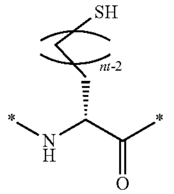

In the structures (t-1) and (t-2), * represents a bonding site to an adjacent amino acid residue, and nt-1 and nt-2 represent an integer of 0 or more.

The nt-1 or nt-2 pieces of carbon atoms in the side chain and the carbon atom at the β-position may be substituted with at least one substituent selected from the group consisting of —$NH_2$, —SH, —COOH, an alkyl group having 1 to 10 carbon atoms, and an aryl group having 6 to 14 carbon atoms.

The alkyl group having 1 to 10 carbon atoms may be either linear or branched. Examples of the alkyl group having 1 to 10 carbon atoms include a methyl group, an ethyl group, an n-propyl group, an isopropyl group, an n-butyl group, an isobutyl group, and a t-butyl group.

In addition, the aryl group having 6 to 14 carbon atoms may be a monocyclic ring or a fused ring. Examples of the aryl group having 6 to 14 carbon atoms include a phenyl group, a naphthyl group, an anthranyl group, and a phenanthrene group.

nt-1 and nt-2 are preferably an integer of 0) to 10, more preferably an integer of 0) to 6, and still more preferably an integer of 1 to 4 due to the ease of forming a thioether bond.

More specific examples of the amino acid having a thiol group on the side chain include cysteine, penicillamine, homocysteine (an amino acid derived from 2-amino-4-mercaptobutanoic acid), and an amino acid derived from 2-amino-5-mercaptopentanoic acid.

Among these, the amino acid having a thiol group on the side chain is preferably an amino acid derived from L-homocysteine, D-homocysteine, L-penicillamine, or D-penicillamine from the viewpoint of bond stability.

From the viewpoints of bond stability and molecule stability; any one of $X^c$ or $X^d$ before the formation of a thioether bond is preferably an amino acid residue derived from an amino acid having a thiol group, more preferably an amino acid residue derived from an amino acid having a thiol group on the side chain, still more preferably an amino acid residue derived from L-homocysteine, D-homocysteine, L-penicillamine, or D-penicillamine, and from the viewpoint that racemization hardly occurs, L-homocysteine or D-homocysteine is even still more preferable.

In a case where $X^a$ is an amino acid residue derived from an amino acid protected by an organic group having a halogen atom, from the viewpoints of bond stability and molecule stability, $X^b$ is preferably an amino acid residue derived from an amino acid having a thiol group, more preferably an amino acid residue derived from an amino acid having a thiol group on the side chain, still more preferably an amino acid residue derived from L-homocysteine, D-homocysteine, L-penicillamine, or D-penicillamine, and from the viewpoint that racemization hardly occurs, L-homocysteine or D-homocysteine is even still more preferable.

In addition, in a case where any one of the amino acid residues $X^a$ and $X^b$, and any one of $X^c$ and $X^d$ are amino acid residues derived from an α-amino acid, the thioether bond may be a thioether bond in which an amino group or modified amino group that is bonded to the α carbon of the α-amino acid before thioether bonding is bonded to a thiol group, or may be a thioether bond in which the side chain of an amino acid residue derived from an α-amino acid before thioether bonding is bonded to a thiol group. In this case, the bonding between the amino group and the thiol group can be carried out through a haloacetyl group or the like positioned on the amino group.

Similarly, in a case where any one of the amino acid residues $X^a$ and $X^b$, and any one of $X^c$ or $X^d$ are amino acid residues derived from an α-amino acid, the thioether bond may be a thioether bond in which a carboxy group or modified carboxy group moiety that is bonded to the α carbon of the α-amino acid before thioether bonding is bonded to a thiol group before thioether bonding, or may be a thioether bond in which the side chain moiety of an amino acid residue derived from an α-amino acid before thioether bonding is bonded to a thiol group before thioether bonding.

[Amino Acid Residue Derived from Amino Acid Protected by Organic Group Having Halogen Atom]

The amino acid residue derived from an amino acid protected by an organic group having a halogen atom is preferably an amino acid residue derived from an amino acid in which an organic group having a halogen atom is bonded to an amino group bonded to the α carbon of an amino acid or an amino acid which has an organic group having a halogen atom in the side chain of an amino acid. The organic group having a halogen atom is not particularly limited as long as it is generally used as a protective group for an amino acid, and suitable examples thereof include a haloacetyl group. For example, in a case where a halogen atom is eliminated and a sulfur atom is bonded instead, a thioether bond is formed, and the above amino acid residue is formed.

Examples of the amino acid in which an organic group having a halogen atom is bonded to an amino group bonded to the α carbon of an amino acid include any amino acid in which a haloalkanoyl group is bonded to the amino group on the α carbon. The haloalkanoyl group is, for example, a haloacetyl group. The halogen atom in the haloalkanoyl group is, for example, a fluorine atom, a chlorine atom, a bromine atom, or an iodine atom. The amino acid to be bonded to an organic group having a halogen atom may be an L-amino acid or a D-amino acid, and examples thereof include isoleucine, lysine, aspartic acid, glutamic acid, tyrosine, leucine, threonine, and valine. Examples of the amino acid in which an organic group having a halogen atom is bonded to an amino group bonded to the α carbon of an amino acid include N-α-chloroacetyl-isoleucine, N-α-chloroacetyl-lysine, N-α-chloroacetyl-aspartic acid, N-α-chloroacetyl-glutamic acid, N-α-chloroacetyl-tyrosine, N-α-chloroacetyl-leucine, N-α-chloroacetyl-threonine, and N-α-chloroacetyl-valine, which may be an L-amino acid or a D-amino acid.

The amino acid residue protected by an organic group having a halogen atom, in the side chain, is preferably an amino acid having an organic group having a halogen atom, at the terminal of the side chain of an amino acid residue from the viewpoint of ease of forming a thioether bond. Suitable examples of the amino acid residue having such an aspect include an amino acid residue represented by the following structure (p-1) or (p-2).

(p-1)

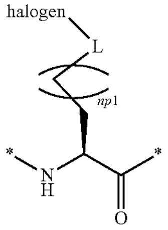

(p-2)

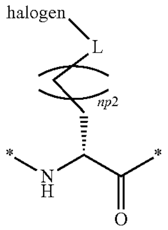

In the formulae (p-1) and (p-2), halogen represents a halogen atom; L represents a divalent linking group represented by $-(CH_2)_{L1}-C(=O)-$ or $-(CH_2)_{L1}-C(=O)-NH-$, where L1 represents an integer of 0 or more and 10 or less; np1 and np2 each independently represent an integer of 0 or more; and * represents a bonding site to an adjacent amino acid residue. np1 and np2 each preferably represent an integer of 0 to 6, more preferably an integer of 0 to 4, and still more preferably an integer of 1 to 3. Further, in L, the halogen is bonded to the left terminal (the terminal on the alkyl side in a case where L1 is 1 or more).

Examples of the halogen atom include a fluorine atom, a chlorine atom, a bromine atom, and an iodine atom. Among these, a bromine atom or a chlorine atom is preferable, and a chlorine atom is more preferable, from the viewpoint of the reactivity, the ease of formation of a thioether bond, and safety.

In a case where np1 and np2 are 1 or more, the np1 or np2 pieces of carbon atom in the side chain and the carbon atom at the β-position may be substituted with at least one substituent selected from the group consisting of an alkyl group having 1 to 10 carbon atoms and an aryl group having 6 to 14 carbon atoms.

L1 is preferably an integer of 0 to 10, more preferably an integer of 1 to 6, and still more preferably an integer of 1 to 3.

Specific examples of the alkyl group having 1 to 10 carbon atoms and the aryl group having 6 to 14 carbon atoms respectively include the alkyl group having 1 to 10 carbon atoms and the aryl group having 6 to 14 carbon atoms in the above specific (t-1) and (t-2).

In a case where the amino acid residue derived from an amino acid protected by an organic group having a halogen atom is located at the N-terminal of the cyclic peptide, from the viewpoint of easiness of forming a thioether bond, the amino acid residue before thioether bonding is preferably an amino acid residue having an organic group having a halogen atom, in the α-amino group, and more preferably an amino acid residue represented by the following structure (r-1).

(r-1)

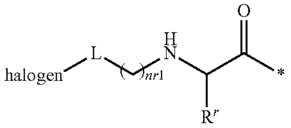

In the formula (r-1), R' represents a hydrogen atom or a monovalent organic group; halogen represents a halogen atom; L represents a divalent linking group represented by $-(CH_2)_{L1}-C(=O)-$ or $-(CH_2)_{L1}-C(=O)-NH-$, where L1 represents an integer of 0 or more and 10 or less; nr1 represents an integer of 0 or more; and * represents a bonding site to an adjacent amino acid residue.

L and L1 are respectively synonymous with L and L1 in the structures (p-1) and (p-2), and the same applies to the preferred embodiments. nr1 is synonymous with np1 and np2 in the structures (p-1) and (p-2), and the same applies to the preferred embodiment.

The monovalent organic group as $R^r$ is not particularly limited, and examples thereof include an aliphatic hydrocarbon group that can be taken as a side chain of an amino acid. Examples of the monovalent organic group that can be taken as a side chain of an amino acid include monovalent organic groups that are the side chains of the amino acids listed in Table 1 or Table 2.

The aliphatic hydrocarbon group may be substituted with at least one substituent selected from the group consisting of $-NH_2$, —SH, —COOH, an alkyl group having 1 to 10 carbon atoms, and an aryl group having 6 to 14 carbon atoms.

The alkyl group having 1 to 10 carbon atoms may be either linear or branched. Examples of the alkyl group having 1 to 10 carbon atoms include a methyl group, an ethyl group, an n-propyl group, an isopropyl group, an n-butyl group, an isobutyl group, and a t-butyl group.

In addition, the aryl group having 6 to 14 carbon atoms may be a monocyclic ring or a fused ring. Examples of the aryl group having 6 to 14 carbon atoms include a phenyl group, a naphthyl group, an anthranyl group, and a phenanthrene group.

In a case where the amino acid residue $X^a$ is located at the N-terminal of the specific amino acid sequence (in a case where m5 of $X_5$ is 0) and is an amino acid residue derived from an α-amino acid, the amino acid residue $X^a$ is preferably an amino acid residue derived from an amino acid represented by the following structure (r).

(r)

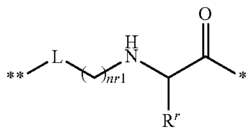

In the formula (r), $R^r$ represents a hydrogen atom or a monovalent organic group; L represents a divalent linking group represented by $—(CH_2)_{L1}—C(=O)—$ or $—(CH_2)_{L1}—C(=O)—NH—$, where L1 represents an integer of 0 or more and 10 or less; nr1 represents an integer of 0 or more; * represents a bonding site to an adjacent amino acid residue; and ** represents a bonding site to a sulfur atom in the thioether bond.

$R^r$, L, and nr1 are respectively synonymous with $R^r$, L, and nr1 in the structure (r-1), and the same applies to the preferred embodiments.

More specific examples of the amino acid residue before thioether bonding, which is derived from an amino acid protected by an organic group having a halogen atom, is not particularly limited; however, examples thereof include amino acid residues derived from 2-amino-3-[(2-haloacetyl)amino]propanoic acid, 2-amino-4-[(2)-haloacetyl)amino]butanoic acid, N-δ-haloacetylornithine, N-ε-haloacetyllysine, 2-[(haloacetyl)amino]-3-methyl-pentanoic acid, and N-ζ-haloacetylhomolysine.

Examples of the halogen atom in the haloacetyl in these amino acid residues include a fluorine atom, a chlorine atom, a bromine atom, and an iodine atom. Among them, a chlorine atom is preferable.

The amino acid residue before thioether bonding, which is derived from an amino acid protected by an organic group having a halogen atom, is preferably an amino acid residue derived from an amino acid having a chloroacetyl group in the side chain, and more preferably an amino acid residue derived from an amino acid selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, N-ε-chloroacetyl-D-lysine, N-ζ-chloroacetyl-L-homolysine, N-ζ-chloroacetyl-D-homolysine, and (2S,3S)-2-[(chloroacetyl)amino]-3-methyl-pentanoic acid, from the viewpoints of bond stability and molecule stability. However, for $X^a$, it is also preferably an amino acid residue derived from an amino acid in which an organic group having a halogen atom is bonded an amino group bonded to the α carbon of an amino acid, such as N-α-chloroacetyl-isoleucine, N-α-chloroacetyl-lysine, N-α-chloroacetyl-aspartic acid, N-α-chloroacetyl-glutamic acid, N-α-chloroacetyl-tyrosine, N-α-chloroacetyl-leucine, N-α-chloroacetyl-threonine, or N-α-chloroacetyl-valine.

From the viewpoints of bond stability and molecule stability, any one of $X^c$ or $X^d$ is preferably an amino acid residue derived from an amino acid protected by an organic group having a halogen atom, more preferably an amino acid residue having an organic group having a chlorine atom on the side chain, still more preferably an amino acid residue having a chloroacetyl group on the side chain, and particularly preferably an amino acid residue derived from an amino acid selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid. (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, N-ε-chloroacetyl-D-lysine, and N-ζ-chloroacetyl-L-homolysine, N-ζ-chloroacetyl-D-homolysine.

In a case where the amino acid residue $X^b$ is an amino acid residue derived from an amino acid having a thiol group, from the viewpoints of bond stability and molecule stability; $X^a$ is preferably an amino acid residue derived from an amino acid in which an organic group having a halogen atom is bonded to an amino group bonded to the α carbon of an amino acid or an amino acid residue derived from an amino acid protected by an organic group having halogen atom, more preferably an amino acid residue derived from an amino acid in which an organic group having a chlorine atom is bonded to an amino group bonded to the α carbon of an amino acid or an amino acid residue having an organic group having a chlorine atom, on the side chain, still more preferably an amino acid residue having a chloroacetyl group on an amino group bonded to α carbon or on a side chain, and even still more preferably an amino acid residue derived from an amino acid selected from the group consisting of N-α-chloroacetyl-isoleucine, N-α-chloroacetyl-lysine, N-α-chloroacetyl-aspartic acid, N-α-chloroacetyl-glutamic acid, N-α-chloroacetyl-tyrosine, N-α-chloroacetyl-leucine, N-α-chloroacetyl-threonine, and N-α-chloroacetyl-valine, or an amino acid residue derived from an amino acid selected from the group consisting of (2S)-2-amino-3-[(2-chloroacetyl)amino]propanoic acid, (2R)-2-amino-3-[(2-chloroacetyl)amino]propanoic acid, (2S)-2-amino-4-[(2-chloroacetyl)amino]butanoic acid, (2R)-2-amino-4-[(2-chloroacetyl)amino]butanoic acid, N-δ-chloroacetyl-L-ornithine, N-δ-chloroacetyl-D-ornithine, N-ε-chloroacetyl-L-lysine, N-ε-chloroacetyl-D-lysine, N-ζ-chloroacetyl-L-homolysine, N-ζ-chloroacetyl-D-homolysine, and (2S,3S)-2-[(chloroacetyl)amino]-3-methyl-pentanoic acid.

[Amino Acid Residues $X^a$ to $X^d$ after Formation of Thioether Bond]

In the amino acid residues $X^a$ to $X^d$ after the formation of a thioether bond, examples of the structure of the amino acid residue after a thioether bond has been formed, where the amino acid residue is derived from an amino acid protected by an organic group bonded to the sulfur atom, include a structure represented by the following structure (q-1) or (q-2).

(q-1)

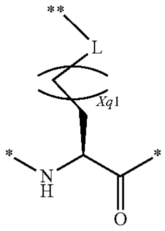

(q-2)

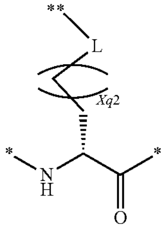

In the structures (q-1) and (q-2), * is a bond to an adjacent amino acid residue; ** is a bond to a sulfur atom of an amino acid residue which is a counterpart in the thioether bond; xq1 and xq2 are each independently an integer of 0 or more; and L's each independently represent a divalent linking group represented by $-(CH_2)_{L1}-C(=O)-$ or $-(CH_2)_{L1}-C(=O)-NH-$, where L1 represents an integer of 0 or more and 10 or less.

L and L1 are respectively synonymous with L and L1 in the structures (p-1) and (p-2), and the same applies to the preferred embodiments. xq1 and xq2 are respectively synonymous with np1 and np2 in the structures (p-1) and (p-2), and the same applies to the preferred embodiments.

More specific examples of the amino acid residue after a thioether bond has been formed, where the amino acid residue is derived from an amino acid protected by an organic group bonded to the sulfur atom, include amino acid residues derived from 2-amino-3-[acetylamino]propanoic acid, 2-amino-4-[acetylamino]butanoic acid, N-δ-acetylornithine, N-ε-acetyllysine, and N-ζ-acetylhomolysine.

However, examples thereof also include amino acid residues derived from N-α-acetyl-isoleucine, N-α-acetyl-lysine, N-α-acetyl-aspartic acid, N-α-acetyl-glutamic acid, N-α-acetyl-tyrosine, N-α-acetyl-leucine, N-α-acetyl-threonine, and N-α-acetyl-valine, since the thioether bond for $X^a$ can be formed from an amino acid in which an organic group having a halogen atom is bonded to an amino group bonded to the α carbon of an amino acid. The acetyl group moiety of these amino acid residues is bonded to the sulfur atom of the thioether bond.

In a case where, among the two amino acid residues involved in the thioether bond, an amino acid residue that does not supply the sulfur atom of the thioether bond is substituted with an alkanoyl group such as an acetyl group, the sulfur atom in the thioether bond is bonded to the alkanoyl group unless otherwise specified, and the alkanoyl group (for example, an acetyl group) can be said to be an S-bonded alkanoyl group (for example, an S-acetyl group). However, in the present disclosure, unless otherwise specified, the description of "S-bonded" in such an S-bonded alkanoyl group is omitted, and it is simply described as the alkanoyl group (for example, the acetyl group).

Among the amino acid residues $X^a$ to $X^d$ after the formation of a thioether bond, examples of the structure of the amino acid residue having a thiol group on the side chain after a thioether bond has been formed, in the amino acid residues $X^a$ to $X^d$ after the formation of a thioether bond, include a structure of an amino acid residue represented by the following structure (t-1) or (t-2).

(t-1)

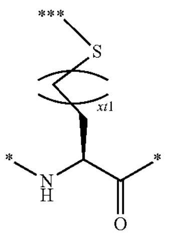

(t-2)

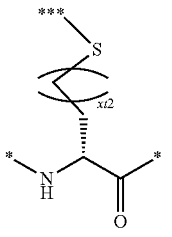

In the structures (t-1) and (t-2), * is a bond to an adjacent amino acid residue, *** is a bond to α carbon atom of an amino acid residue which is a counterpart in the thioether bond, and xt1 and xt2 are each independently an integer of 0 or more.

xt1 and xt2 are respectively synonymous with np1 and np2 in the structures (p-1) and (p-2), and the same applies to the preferred embodiments.

More specific examples of the amino acid residue having a thiol group on the side chain after a thioether bond has been formed include a cysteine residue, a penicillamine residue, a homocysteine residue (a residue derived from 2-amino-4-mercaptobutanoic acid), and an amino acid residue derived from 2-amino-5-mercaptopentanoic acid.

The amino acid residue derived from an amino acid protected by an organic group bonded to the sulfur atom, such as an amino acid residue of the structure (q-1) or (q-2), may be the amino acid residue $X^a$ or $X^c$, each of which is on the N-terminal side in the cyclic segment, or may be the amino acid residue $X^b$ or $X^d$, each of which is on the C-terminal side in the cyclic segment. Correspondingly to the above, the amino acid residue having a thiol group, such as the amino acid residue of (t-1) or (t-2), may be the amino acid residue $X^a$ or $X^c$ on the N-terminal side in the cyclic segment or may be the amino acid residue $X^b$ or $X^d$ on the C-terminal side in the cyclic segment.

The amino acid residue represented by the structural formula (p-1) or (p-2) may be an amino acid residue having a structure selected from the amino acid residues represented by the following structures (a) to (h).

(a)

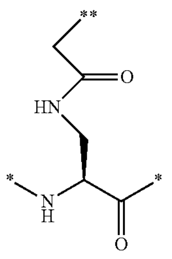

(b)

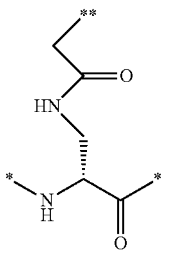

(c)

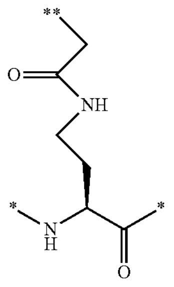

-continued (d)

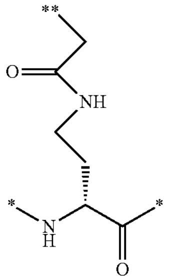

(e)

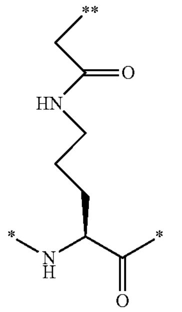

(f)

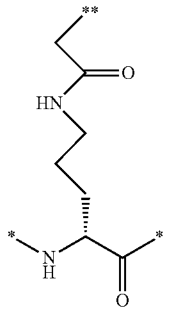

(g)

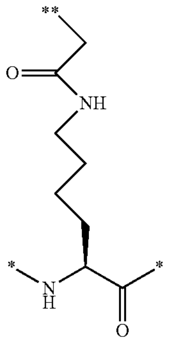

(h)

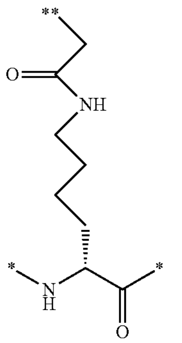

Here, in the formulae, * is a bond to an adjacent amino acid residue, and ** is a bond to a sulfur atom of an amino acid residue which is a counterpart in the thioether bond.

From the viewpoint of molecule stability, in a case where any one of the amino acid residue $X^c$ and the amino acid residue $X^d$ is a cysteine residue, it is preferable to design so that the α carbon of the other amino acid residue of the amino acid residue $X^c$ and the amino acid residue $X^d$ and the cysteine residue are separated by 5 or more atoms from the viewpoint that a further improved molecule stability is obtained. Although it is not clear why further improved molecule stability can be obtained, it is presumed that the electron arrangement in the thioether bond is stabilized by increasing the carbon chain length from the sulfur atom of the amino acid residue which is a counterpart in the thioether bond to the cyclic peptide main chain, and thus a high bond stability is obtained. The same applies to a case where any one of the amino acid residue $X^a$ and the amino acid residue $X^b$ is a cysteine residue, and the other is an amino acid residue in which the sulfur atom of the thioether bond is bonded to the amino acid side chain through an organic group.

In the amino acid residue derived from an amino acid having a thiol group among the amino acid residue $X_a$ and the amino acid residue $X^b$, the total number of carbon atoms on the side chain having a thiol group is preferably 1 to 10, more preferably 1 to 6, still more preferably 1 to 4, and particularly preferably 2 to 4, from the viewpoint of obtaining a higher molecule stability.

In the amino acid residue derived from an amino acid having a thiol group, the total number of carbon atoms on the side chain having a thiol group is the total number of carbon atoms in the side chain having a thiol group. However, the total number of carbon atoms on the side chain having a thiol group does not include the number of carbon atoms contained in the main chain.

For example, in the cysteine residue, the total number of carbon atoms on the side chain having a thiol group is 1; in the homocysteine residue, the total number of carbon atoms on the side chain having a thiol group is 2; and in the penicillamine residue shown below, the total number of carbon atoms on the side chain is 3. Here, * in the penicillamine residue shown below indicates a bonding site to an adjacent amino acid residue.

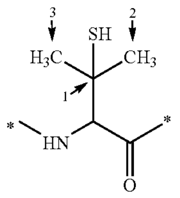

In addition, in the amino acid residue having a thiol group, the chain length between the main chain of the cyclic peptide and the sulfur atom in the side chain having a thiol group is preferably 1 to 10 carbon atoms, more preferably 1 to 6 carbon atoms, still more preferably 1 to 4 carbon atoms, and particularly preferably 1 to 3 carbon atoms, from the viewpoint of integrin binding property.

The chain length between the main chain of the cyclic peptide and the sulfur atom in the side chain having a thiol group is a value counted so that the number of atoms of the side chain connecting the main chain and the thiol group in the cyclic peptide is minimized, and carbon atoms contained in the main chain are not included in the number for chain length.

For example, in a case where the amino acid residue having a thiol group is the penicillamine residue shown below, the chain length between the main chain of the cyclic peptide and the sulfur atom in the side chain having a thiol group is 1. Here, * in the penicillamine residue shown below indicates a bonding site to an adjacent amino acid residue.

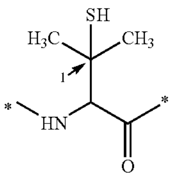

For example, in a case of an amino acid residue derived from an α-amino acid having a thiol group, the chain length between the main chain of the cyclic peptide and the sulfur atom in the side chain having a thiol group is preferably 1 to 10, more preferably 1 to 6, still more preferably 1 to 4, and particularly preferably 1 to 3, from the viewpoint of integrin binding property.

In terms of the chain length between the α carbon of an amino acid residue that does not supply the sulfur atom of the thioether bond and the sulfur atom of an amino acid residue that supplies the sulfur atom of the thioether bond, among the amino acid residue $X^a$ and the amino acid residue $X^b$, they are preferably separated by 4 or more atoms, more preferably separated by 4 to 9 atoms, and still more preferably separated by 4 to 8 atoms, from the viewpoint of obtaining a higher molecule stability. However, this does not apply in a case where $X^a$ is an amino acid residue in which the sulfur atom of the thioether bond is bonded to the amino group on the α-carbon through an organic group.

From the same viewpoint, in terms of the chain length between the α carbon of an amino acid residue that does not supply the sulfur atom of the thioether bond and the sulfur atom of an amino acid residue that supplies the sulfur atom of the thioether bond, among the amino acid residue $X^c$ and the amino acid residue $X^d$, they are preferably separated by 4 or more atoms, more preferably separated by 4 to 9 atoms, and still more preferably separated by 4 to 8 atoms.

As an example of the case where, in terms of the chain length between the α carbon of the amino acid residue that does not supply the sulfur atom of the thioether bond and the sulfur atom of the amino acid residue that supplies the sulfur atom of the thioether bond, they are separated by 4 or more atoms, a case where the amino acid residue of the (a) is bonded to the L-cysteine residue is exemplified; however, the present disclosure is not limited thereto.

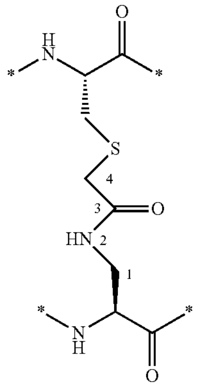 [SMILES: *N[C@@H](CNC(=O)CSC[C@H](N*)C(*)=O)C(*)=O]

Here, in the formulae, * is a bonding site to an adjacent amino acid residue. In a case where the amino acid residue of (a) is bonded to the L-cysteine residue, the α carbon and the sulfur atom of the cysteine residue are separated, in terms of the chain length, by one nitrogen atom and three carbon atoms, and thus the number of atoms is four atoms. As described above, the number (the chain length) of atoms separating the α carbon of the amino acid residue which is a counterpart in the thioether bond from the sulfur atom of the cysteine residue means the number of atoms on a chain connecting the α atom and the sulfur atom, and atoms that do not participate in the chain, such as hydrogen atoms bonded to the atom on the chain are not counted.

<<Method of Forming Thioether Bond>>

The method of forming a thioether bond between the amino acid residue $X^c$ and the amino acid residue $X^d$, and between the amino acid residue $X^a$ and the amino acid residue $X^b$ before the formation of a thioether bond is particularly limited; however, examples thereof include a known method of forming a thioether bond in a peptide.

Regarding the thioether bond, it is possible to form a thioether bond, for example, by reacting an amino acid residue having a thiol group with an amino acid residue protected by an organic group having a halogen atom under the neutral or alkaline conditions (pH 7 to pH 9), thereby the sulfur atom in the thiol group being bonded to the organic group with the generation of a hydrogen halide.

Suitable examples of the organic group having a halogen atom include a protective group such as a haloacetyl group.

In addition, examples of the method of forming a thioether bond by reacting a thiol group with an organic group having a halogen, between an amino acid residue having a thiol group on the side chain and an amino acid residue to which an organic group having a halogen atom is bonded to an amino group bonded to the α carbon atom of an amino acid or an amino acid residue having an organic group having a halogen on the side chain, include, for example, a method of forming a thioether bond by reacting a linear peptide before cyclization in a neutral or basic buffer solution.

More specific suitable examples thereof include a method in which an aqueous solution containing a linear peptide is slowly added dropwise to a Tris-HCl (pH 8.5) buffer solution and allowed to stand. In the cyclization reaction in which a thioether bond is formed, in addition to the cyclic peptide, an oligomer in which a plurality of noncyclic peptides are connected by intermolecular bonding may be formed depending on the reaction conditions. The method of forming a thioether bond preferably includes a purification step from the viewpoint of improving the yield of a cyclic peptide. Examples of the method of purifying a cyclic peptide include known purification methods. The method of purifying the cyclic peptide is preferably a method of purifying the peptide after the cyclization reaction by reverse phase high performance liquid chromatography or the like.

<<Amino acid residues $X_1$ to $X_5$>>

In the specific amino acid sequence, $X_1$ to $X_5$ each independently represent an amino acid residue, and m1 to m5 each independently represent an integer of 0 or more.

The numbers m1 to m5 of the respective amino acid residues $X_1$ to $X_5$ are not particularly limited as long as the total number of amino acid residues represented by $X^a$, $X^b$, $X^c$, and $X^d$ and represented by $X_1$, $X_3$, and $X_4$, and RGD is in a range of 7 to 16.

The amino acid residues are not particularly limited as long as a cyclic peptide can be formed. Here, the amino acid residue is preferably an amino acid residue derived from an amino acid selected from the group consisting of the amino acids (excluding B, Z, and X) listed in Table 1 and the amino acids listed in Table 2, and it is more preferably an amino acid residue derived from an amino acid selected from the group consisting of the amino acids (excluding B, Z, and X) listed in Table 1.

In addition, an amino acid residue derived from an enantiomer or a diastereomer of the above amino acid, in a case of being present, may also be used.

In the specific amino acid sequence, regarding $X_1$ to $X_5$, any two amino acid residues selected from the group consisting of $X_1$ to $X_5$ may form a thioether bond with each other.

Examples of the combination of amino acid residues capable of forming a thioether bond include a combination in which one of $X^c$ and $X^d$ is an amino acid residue derived from an amino acid having a thiol group, and the other is an amino acid residue derived from an amino acid protected by an organic group having a halogen atom.

The amino acid residue derived from an amino acid having a thiol group and the amino acid residue derived from an amino acid protected by an organic group having a halogen atom are respectively synonymous with the amino acid residue derived from an amino acid having a thiol group in the amino acid residues $X^a$ to $X^d$ and the amino acid residue derived from an amino acid protected by an organic group having a halogen atom, and the same applies to the preferred embodiment.

The above amino acid residue may be, for example, an amino acid residue having a carboxy group in the side chain, an amino acid residue having a hydroxy group in the side chain, or the like.

Examples of the amino acid residue having a carboxy group in the side chain include an L-aspartic acid residue, a D-aspartic acid residue, an L-glutamic acid residue, a D-glutamic acid residue, an L-homoglutamic acid residue, and a D-homoglutamic acid residue.

Examples of the amino acid residue having a hydroxy group in the side chain include an L-serine residue, a D-serine residue, an L-homoserine residue, a D-homoserine residue, an L-tyrosine residue, a D-tyrosine residue, an L-threonine residue, a D-threonine residue, an L-allothreonine residue, and a D-allothreonine residue.

The above amino acid residue may be, for example, a hydrophobic amino acid residue.

Examples of the hydrophobic amino acid residues include amino acid residues such as valine, methionine, tryptophan, proline, leucine, phenylalanine, isoleucine, alanine, and glycine.

<<Amino Acid Residue Represented by $X_1$>>

The amino acid residue represented by $X_1$ is preferably at least one of an amino acid residue derived from a hydrophobic amino acid or an amino acid residue having a ring structure, still more preferably an amino acid residue derived from tyrosine, phenylalanine, 3-iodotyrosine, naphthylalanine, homotyrosine, proline, or isoleucine, and particularly preferably an amino acid residue derived from phenylalanine or tyrosine, from the viewpoint of integrin binding property.

The number m1 of amino acid residues represented by $X_1$ is an integer of 0 or more and is preferably 1 or more and 6 or less, more preferably 1 or more and 3 or less, and still more preferably 1 or 2, from the viewpoint of cost.

<<Number m3 and m4 of Amino Acid Residues Respectively Represented by $X_3$ and $X_4$>>

The amino acid residues respectively represented by $X_3$ and $X_4$ are not particularly limited; however, from the viewpoint of integrin binding property, they are preferably an amino acid residue of proline, threonine, or asparagine, serine, homoserine, valine, or alanine.

In addition, the numbers m3 and m4 of amino acid residues respectively represented by $X_3$ and $X_4$ are each independently an integer of 0 or more. From the viewpoint of cost, m3 and m4 are each independently preferably 0 or more and 2 or less and more preferably 0 or more and 1 or less, and still more preferably both m3 and m4 are 0.

In a case where the number m3 and m4 of amino acid residues respectively represented by $X_3$ and $X_4$ is 2 or more, $X_3$ and $X_4$ may be the same amino acid residue or may be amino acid residues different from each other.

<<Amino Acid Residues Represented by $X_2$ and $X_5$>>

The numbers m2 and m5 of amino acid residues respectively represented by $X_2$ and $X_5$ are each independently an integer of 0 or more. From the viewpoint of cost, m5 is preferably 0. Due to molecule stability and the ease of forming a covalent bond by a reaction with a functional group on a base material or a holding material described later, m2 is preferably 1 or more, more preferably 1 or more and 6 or less, and still more preferably 1 or more and 4 or less.

In a case where m5 is 0, the amino acid residue represented by $X^a$ may be an amino group or a modified amino group.

In a case where the number m2 of amino acid residues represented by $X_2$ is 2 or more, $X_2$'s may be the same amino acid residues with each other or may be amino acid residues different from each other; however, $X_2$'s is preferably the same amino acid residues with each other.

<<Amino Acid Having Immobilizing Functional Group in Side Chain>>

The amino acid residues respectively represented by $X_5$ and $X_2$ preferably include an amino acid residue (hereinafter, also simply referred to as an "amino acid residue having an immobilizing functional group") having an immobilizing functional group in the side chain due to molecule stability and the ease of forming a covalent bond by a reaction with a functional group on a base material or a holding material described later.

The above-described "immobilizing functional group" refers to a functional group capable of forming a covalent bond by reacting with a functional group on a base material or a holding material, which will be described later.

Examples of the immobilizing functional group include an amino group, a carboxy group, a hydroxy group, a thiol group, an aldehyde group (a formyl group), a carbamoyl group, an azide group, and an alkynyl group.

The immobilizing functional group in the amino acid having the above immobilizing functional group is preferably at least one group selected from the group consisting of an amino group, a thiol group, and an aldehyde group, and more preferably at least one group selected from the group consisting of an amino group and a thiol group, from the viewpoint of reactivity with the functional group on the base material or the holding material.

In a case where an amino group is used as the immobilizing functional group, the amino group can be bonded to the carboxy group on the base material or the holding material through an amide bond, and thus the cyclic peptide according to the present disclosure can be easily immobilized on the base material or the holding material.

In addition, in a case where a thiol group is used as the immobilizing functional group, the thiol group can be bonded to the epoxy group on the base material or the holding material through a covalent bond, and thus the cyclic peptide according to the present disclosure can be easily immobilized on the base material or the holding material.

Examples of the amino acid residue having an amino group in the side chain include an L-lysine residue and a D-lysine residue. Examples of the amino acid residue having a thiol group in the side chain include an L-cysteine residue and a D-cysteine residue. Since the amino acid residue having an amino group in the side chain and the amino acid residue having a thiol group in the side chain can be introduced at a relatively low cost, the production cost of the cyclic peptide according to the present disclosure can be suppressed. For this reason, the use of the above amino acid residues is preferable from an economical viewpoint.

That is, the amino acid having an immobilizing functional group in the side chain is preferably at least one amino acid selected from the group consisting of an L-lysine, a D-lysine, an L-cysteine, a D-cysteine, an L-homocysteine, and a D-homocysteine, and more preferably at least one amino acid selected from the group consisting of an L-lysine and D-lysine, from the viewpoint of molecule stability.

From the viewpoint of immobilization to the base material or the like, it is preferable that at least one of $X_5$ (the N-terminal of the cyclic peptide) or $X_2$ (the C-terminal of the cyclic peptide) contains a lysine residue as the amino acid residue having an immobilizing functional group, and it is more preferable that $X_2$ contains a lysine residue as the amino acid residue having an immobilizing functional group.

From the viewpoint of immobilization to the base material or the like, at least one of $X_5$ (the N-terminal of the cyclic peptide) or $X_2$ (the C-terminal of the cyclic peptide) preferably contains consecutively one or more lysine residues as the amino acid residues having an immobilizing functional group, more preferably contains consecutively 2 to 10 lysine residues, and still more preferably contains consecutively 2 to 5 lysine residues.

$X_5$ (the N-terminal of the cyclic peptide) and $X_2$ (the C-terminal of the cyclic peptide) may be composed of only consecutive amino acid residues having an immobilizing functional group (preferably lysine residues); however, they may contain an amino acid residue other than the amino acid residue having an immobilizing functional group.

The amino acid residue other than the amino acid residue having an immobilizing functional group may be amino acid residues of 1 to 20 residues, 1 to 10 residues, 1 to 5 residues, or 1 to 3 residues, selected from an alanine residue, a β-alanine residue, a glutamic acid residue, an aspartic acid residue, and a glycine residue.

Further, a lysine residue may further reside between the above amino acid residue other than the amino acid residue having an immobilizing functional group and $X^a$ or $X^b$.

Examples of the combination of the immobilizing functional group contained in the cyclic peptide according to the present disclosure and the functional group on the base material or the holding material include, which are not particularly limited, a combination of an amino group and a carboxy group, a combination of an amino group and an aldehyde group, a combination of an amino group and an epoxy group, a combination of a hydroxy group and an epoxy group, a combination of a carboxy group and a hydroxy group, a combination of a thiol group and an epoxy group, and a combination of an azide group and an alkynyl group.

The immobilizing functional group contained in the cyclic peptide according to the present disclosure reacts with a functional group on the base material or the holding material to form a covalent bond, whereby the cyclic peptide according to the present disclosure is immobilized on the base material or the holding material.

Here, it is sufficient that at least a part of the immobilizing functional groups contained in the cyclic peptide according to the present disclosure reacts with the functional group on the base material or the holding material to form a covalent bond, and all the immobilizing functional groups do not have to react with the functional groups on the base material or the holding material.

<<RGD Sequence>>

The specific amino acid sequence contained in the cyclic peptide according to the present disclosure has an RGD sequence, and the RGD sequence is positioned between $X^c$ and $X^d$, which are amino acid residues crosslinked by a thioether bond, and thus an excellent integrin binding property and an excellent molecule stability are exhibited.

In the present disclosure, the "RGD sequence" refers to a sequence in which three amino acid residues of "arginine (R)", "glycine (G)", and "aspartic acid (D)" are present from the N-terminal side to the C-terminal side. Since the "RGD sequence" is involved in cell adhesion, the cyclic peptide according to the present disclosure can enhance particularly the binding property to a cell adhesion molecule such as integrin due to having the "RGD sequence".

In the specific amino acid sequence contained in the cyclic peptide according to the present disclosure, the number of "RGD sequences" may be 2 or more; however, it is preferably 1.

The RGD sequence is located between the amino acid residue $X^c$ and the amino acid residue $X^d$ from the viewpoint of integrin binding property: The position of the RGD sequence may be a position adjacent to the amino acid residue $X^c$ or the amino acid residue $X^d$, or the position thereof may be a position adjacent neither to the amino acid residue $X^c$ nor the amino acid residue $X^d$.

From the viewpoint of integrin binding property, the position thereof is preferably a position corresponding to the 3rd to 5th amino acid residue in a case where amino acid residues are counted toward the C-terminal side with $X_5$ present at the N-terminal in the specific amino acid sequence being set as the first amino acid residue.

The total number of amino acid residues represented by $X^a$, $X^b$, $X^c$, and $X^d$ and represented by $X_1$, $X_3$, and $X_4$, and RGD is 7 to 16. In a case where the total number of amino acid residues represented by $X^a$, $X^b$, $X^c$, and $X^d$ and represented by $X_1$, $X_3$, and $X_4$, and RGD, that is, the number (hereinafter, may be referred to as the number of amino acid residues in the "outermost cyclic segment") of amino acid residues between the most N-terminal amino acid residue ($X^a$) and the most C-terminal amino acid residue ($X^b$) crosslinked by a thioether bond in the crosslinked peptide is 7 to 16, the intramolecular strain of the cyclic peptide does not become too large, the higher-order structure such as α-helix is stabilized, and the integrin binding property is excellent.

From the above viewpoint, the number of amino acid residues in the outermost cyclic segment is preferably 7 to 14 and more preferably 7 to 13.

In addition, the total number of amino acid residues represented by $X^c$ and $X^d$, and $X_3$ and $X_4$, and RGD, that is, the number (hereinafter, may be referred to as the number of amino acid residues in the "innermost cyclic segment") of amino acid residues between the amino acid residue ($X^c$) and the amino acid residue ($X^d$) crosslinked by a thioether bond in the crosslinked peptide, is preferably 5 to 14, more preferably 5 to 10, and still more preferably 5 to 8.

The total number of amino acid residues contained in the amino acid sequence of the cyclic peptide according to the present disclosure is not particularly limited, and it may be 7 to 50 amino acid residues, may be 7 to 30 amino acid residues, may be 8 to 20 amino acid residues, and may be 9 to 15 amino acid residues. The shorter the total length of the cyclic peptide, the lower the risk of antigenicity and the easier the peptide synthesis.

<<Amino Acid Sequence Represented by Formula (2)>>

The amino acid sequence (the specific amino acid sequence) represented by Formula (1), contained in the cyclic peptide according to the present disclosure, is preferably an amino acid sequence represented Formula (2) from the viewpoint of integrin binding property and molecule stability.

(2)

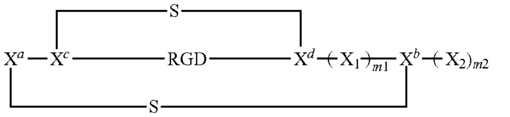

In Formula (2), $X^a$ and $X^b$, and $X^c$ and $X^d$ each independently represent amino acid residues crosslinked through a thioether bond; $X_1$ and $X_2$ each independently represent an amino acid residue; R represents arginine; G represents glycine; D represents aspartic acid; and m1 and m2 each independently represent an integer of 1 or more. However, the total number of amino acid residues represented by $X^a$, $X^b$, $X^c$, and $X^d$ and represented by $X_1$, and RGD is 7 to 14.

In Formula (2), $X^a$, $X^b$, $X^c$, $X^d$, $X_1$, $X_2$, m1, and m2 are respectively synonymous with $X^a$, $X^b$, $X^c$, $X^d$, $X_1$, $X_2$, m1, and m2 in Formula (1), and the same applies to the preferred embodiments.

From the viewpoints of bond stability and molecule stability, it is preferable that any one of $X^c$ or $X^d$ in Formula (2) is an amino acid residue derived from an amino acid having an acetyl group in a side chain, which is selected from the group consisting of (2S)-2-amino-3-[(2-acetyl)amino]propanoic acid, (2R)-2-amino-3-[(2-acetyl)amino]propanoic acid, (2S)-2-amino-4-[(2-acetyl)amino]butanoic acid, (2R)-2-amino-4-[(2-acetyl)amino]butanoic acid, N-δ-acetyl-L-ornithine, N-δ-acetyl-D-ornithine, N-ε-acetyl-L-lysine, N-ε-acetyl-D-lysine, N-ζ-acetyl-D-homolysine, and N-ζ-acetyl-D-homolysine, and the other is an amino acid residue derived from L-homocysteine, D-homocysteine, L-penicillamine, or D-penicillamine. An amino acid residue derived from L-homocysteine or D-homocysteine is more preferable.

From the viewpoints of bond stability and molecule stability, it is preferable that in Formula (2), $X^b$ is an amino acid residue derived from L-homocysteine, D-homocysteine, L-penicillamine, or D-penicillamine, and $X^a$ is an amino acid residue derived from an amino acid selected from the group consisting of (2S)-2-amino-3-[(2-acetyl)amino]propanoic acid, (2R)-2-amino-3-[(2-acetyl)amino]propanoic acid, (2S)-2-amino-4-[(2-acetyl)amino]butanoic acid, (2R)-2-amino-4-[(2-acetyl)amino]butanoic acid, N-δ-acetyl-L-ornithine, N-δ-acetyl-D-ornithine, N-ε-acetyl-L-lysine, N-ε-acetyl-D-lysine, N-ζ-acetyl-L-homolysine, N-ζ-acetyl-D-homolysine, and (2S,3S)-2-[(acetyl)amino]-3-methyl-pentanoic acid.

In Formula (2), the amino acid residue $X^a$ is preferably an amino acid residue represented by the following structure (r) from the viewpoints of bond stability and molecule stability.

(r)

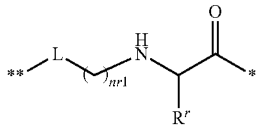

In the formula (r), $R^r$ represents a hydrogen atom or a monovalent organic group; L represents a divalent linking group represented by $-(CH_2)_{L1}-C(=O)-$ or $-(CH_2)_{L1}-C(=O)-NH-$, where L1 represents an integer of 0 or more and 10 or less; nr1 represents an integer of 0 or more; * represents a bonding site to an adjacent amino acid residue; and ** represents a bonding site to a sulfur atom in the thioether bond.

$R^r$, L, and nr1 are respectively synonymous with $R^r$, L, and nr1 in the structure (r-1), and the same applies to the preferred embodiments.

From the viewpoints of bond stability and molecule stability, it is preferable that any one of $X^c$ or $X^d$ in Formula (2) is an amino acid residue derived from an amino acid having an acetyl group in a side chain, which is selected from the group consisting of (2S)-2-amino-3-[(2-acetyl)amino]propanoic acid, (2R)-2-amino-3-[(2-acetyl)amino]propanoic acid, (2S)-2-amino-4-[(2-acetyl)amino]butanoic acid, (2R)-2-amino-4-[(2-acetyl)amino]butanoic acid, N-δ-acetyl-L-ornithine, N-δ-acetyl-D-ornithine, N-ε-acetyl-L-lysine, N-ε-acetyl-D-lysine, N-ζ-acetyl-L-homolysine, and N-ζ-acetyl-D-homolysine, and the other is an amino acid residue derived from L-homocysteine, D-homocysteine, L-penicillamine, or D-penicillamine and that in Formula (2), $X^b$ is an amino acid residue derived from L-homocysteine, D-homocysteine, L-penicillamine, or D-penicillamine, and $X^a$ is an amino acid residue represented by the above structure (r) (more preferably an amino acid residue derived from an amino acid selected from the group consisting of (2S)-2-amino-3-[(2-acetyl)amino]propanoic acid, (2R)-2-amino-3-[(2-acetyl)amino]propanoic acid, (2S)-2-amino-4-[(2-acetyl)amino]butanoic acid, (2R)-2-amino-4-[(2-acetyl)amino]butanoic acid, N-δ-acetyl-L-ornithine, N-δ-acetyl-D-ornithine, N-ε-acetyl-L-lysine, N-ε-acetyl-D-lysine, N-ζ-acetyl-L-homolysine, N-ζ-acetyl-D-homolysine, and (2S,3S)-2-[(acetyl)amino]-3-methyl-pentanoic acid).

The total number of amino acid residues represented by $X^a$, $X^b \cdot X^c$, and $X^d$ and represented by $X_1$, and RGD is 7 to 14. From the viewpoint that the intramolecular strain of the cyclic peptide does not become too large, the higher-order structure such as α-helix is stabilized, and the integrin binding property is excellent, the total number of amino acid residues represented by $X^a$, $X^b$, $X^c$, and $X^d$ and represented by $X_1$, and RGD is preferably 7 to 13 and more preferably 8 to 10.

In addition, from the above viewpoint, the total number of amino acid residues represented by $X^c$ and $X^d$ and RGD is preferably 5.

In Formula (2), the following embodiment is also preferable. Here, each amino acid residue may be an L-amino acid residue or a D-amino acid residue.

That is, $X^a$ is preferably the N-terminal amino acid residue of the cyclic peptide. In this case, $X^a$ may be an amino acid residue derived from isoleucine, lysine, aspartic acid, glutamic acid, tyrosine, leucine, threonine, or valine, in which an acetyl group is bonded to the α carbon. Among the above, an amino acid residue derived from aspartic acid in which an acetyl group is bonded to the α carbon and an amino acid residue derived from glutamic acid in which an acetyl group is bonded to the α carbon is preferable, and a glutamic acid residue in which an acetyl group is bonded to the α carbon is more preferable.

$X^b$ may be an amino acid residue derived from cysteine, an amino acid residue derived from penicillamine, or an amino acid residue derived from homocysteine. Among the above, an amino acid residue derived from homocysteine is preferable.

Among $X^c$ and $X^d$, the amino acid residue that does not supply the sulfur atom of a thioether bond may be an amino acid residue derived from 2-amino-3-[(2-acetyl)amino]propanoic acid, 2-amino-4-[(2-acetyl)amino]butanoic acid, N-δ-acetyl-ornithine, N-ε-acetyl-lysine, or N-ζ-acetyl-homolysine. Among the above, an amino acid residue derived from N-δ-acetyl-ornithine or an amino acid residue derived from N-ε-acetyl-lysine is preferable, and an amino acid residue derived from N-ε-acetyl-lysine is more preferable.

Among $X^c$ and $X^d$, the amino acid residue that supplies the sulfur atom of a thioether bond may be an amino acid residue derived from cysteine, an amino acid residue derived from penicillamine, or an amino acid residue derived from homocysteine. Among the above, an amino acid residue derived from homocysteine is preferable.

$(X_1)_{m1}$ preferably represents F as a whole or $FX^g$. Here, $X^g$ represents any one of amino acid residues, and examples thereof include alanine and arginine.

$(X^2)_{m2}$ preferably contains 3 or more consecutive residues of K. The upper limit of the number of repetitions of K is not particularly limited; however, it may be, for example, 10, 6, or 4. $(X_2)_{m2}$ may represent as a whole, for example, A, K, KKK, AKKK (SEQ ID NO: 50), or the like.

In one preferred embodiment, $X^a$ is an amino acid residue derived from any amino acid in which an acetyl group is bonded to an α carbon; $X^b$ is an amino acid residue derived from homocysteine; $X^c$ is an amino acid residue derived from homocysteine; $X^d$ is an amino acid residue derived from N-δ-acetyl-ornithine or an amino acid residue derived from N-ε-acetyl-lysine; and $(X_1)_{m1}$ is F as a whole. In this case, $X^a$ is preferably an amino acid residue derived from isoleucine, lysine, aspartic acid, glutamic acid, tyrosine, leucine, threonine, or valine, in which an acetyl group is bonded to the α carbon. In addition, $(X_2)_{m2}$ may be as a whole, for example, A, K, KKK, AKKK (SEQ ID NO: 50), or the like.

In another preferred embodiment, $X^a$ is an amino acid residue derived from any amino acid in which an acetyl group is bonded to an α carbon, $X^b$ is an amino acid residue derived from homocysteine, $X^c$ is an amino acid residue derived from N-δ-acetyl-ornithine or an amino acid residue derived from N-ε-acetyl-lysine, $X^d$ is an amino acid residue derived from homocysteine, and $(X_1)_{m1}$ is F as a whole. In this case, $X^a$ is preferably an amino acid residue derived from isoleucine, lysine, aspartic acid, glutamic acid, tyrosine, leucine, threonine, or valine, in which an acetyl group is bonded to the α carbon. In addition, $(X_2)_{m2}$ may be as a whole, for example, A, K, KKK, AKKK (SEQ ID NO: 50), or the like.

Further, the cyclic peptide according to the present disclosure may be a cyclic peptide having a structure in which an additional amino acid is added to the N-terminal of the cyclic peptide of Formula (2) above. The structure of such a cyclic peptide can be represented by Formula (3).

(3)

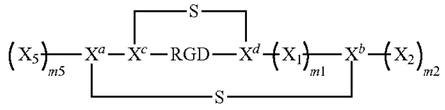

Here, $X^a$, $X^b$, $X^c$, $X^d$, $X_1$, $X_2$, m1, and m2 in Formula (3) are respectively synonymous with $X^a$, $X^b$, $X^c$, $X^d$, $X_1$, $X_2$, m1, and m2 in Formula (2), and the same applies to the preferred embodiments. Further, $X_5$ and m5 are respectively synonymous with $X_5$ and m5 in Formula (1), and the same applies to the preferred embodiments.

However, in the cyclic peptide of Formula (3), $X^a$ is not an amino acid residue in which the sulfur atom of the thioether bond is bonded to the amino group on the α-carbon through an organic group. As a result, examples of the combination and preferred examples of $X^a$ and $X^b$ respectively include the examples of the combination of $X^c$ and $X^d$ in the description of Formula (2) and the amino acid residues exemplified as the preferred example. Which of $X^a$ and $X^b$ is the amino acid residue that supplies the sulfur atom of a thioether bond is not particularly limited; however, it may be, for example, $X^a$.

$(X_5)_{m5}$ may be as a whole, for example, A, K, KKK, AKKK (SEQ ID NO: 50), or the like.

In the cyclic peptide according to the present disclosure, the dissociation constant measured by the method described in "(2) Immobilization of cyclic peptide" and "(3) Evaluation of integrin binding property" in Examples is preferably 200 nM (M: mol/L) or less, more preferably 100 nM or less, and still more preferably 50 nM or less. The closer to 0 nM the dissociation constant is, the more preferable it is; however, from the practical viewpoint, 0.1 nM or 0.5 nM may be used as the lower limit value that can be combined with the above upper limit value include. In addition, the cyclic peptide according to the present disclosure preferably has a residual rate of 30% or more, more preferably 50% or more, and still more preferably 70% or more, where the residual rate is measured by the method described in "(4) Evaluation of molecule stability" in Examples. The closer to 100% the residual rate is, the more preferable it is. For this reason, as the upper limit value that can be combined with the above lower limit value, 100% may be used.

The integrin in the present disclosure is not particularly limited as long as it is an integrin that recognizes the RGD sequence. In Examples described later, the binding property is evaluated using integrin αvβ5; however, the integrin is not limited thereto, and the cyclic peptide according to the present disclosure can bind to an integrin that recognizes an RGD sequence of αVβ3.

In addition, the molecule stability of the cyclic peptide according to the present disclosure is measured by using the alkali resistance as an indicator; however, the molecule stability of the cyclic peptide according to the present disclosure is exhibited similarly for the resistance to stimuli other than alkali, such as X ray resistance, γ ray resistance, ultraviolet ray resistance, heat resistance, and chemical resistance. For example, due to having excellent alkali resistance, in a case where the cyclic peptide according to the present disclosure is used as an affinity ligand in a carrier for affinity chromatography and the carrier is used for cell purification, the integrin binding property is maintained even in a case of being repeatedly washed with alkali, and thus the cell separation cost can be reduced.

Examples of the cyclic peptide according to the present disclosure are shown in Table 3-1 and Table 3-2 below: In all cyclic peptides 1 to 47 shown in Table 3-1 and Table 3-2, all amino acid residues are amino acid residues that do not have an optical isomer, such as an L-amino acid residue and glycine. In the table, Hcy represents a homocysteine residue, Dab (acetyl) represents a 2-amino-4-acetylamino-butanoic acid residue, Dap (acetyl) represents a 2-amino-3-acetylamino-propanoic acid residue, Orn (acetyl) represents an N-δ-acetyl-ornithine residue, and K (acetyl) represents an N-α-acetyl-lysine residue.

One of hydrogen atoms on the methyl group in the acetyl group in the amino acid residue containing the above acetyl group is substituted with a bond to the sulfur atom in the amino acid residue, which is a bonding partner in the thioether bond, whereby crosslinking by the thioether bond is formed. In addition, in the column of "Crosslinking moiety amino acid residue", the acetyl group is omitted.

In Table 3-1 and Table 3-2, the amino acid residues shown in parentheses and the amino acid residues described in the bold font indicate amino acid residues crosslinked by the thioether bond. In addition, the amino acid residues described in the italic font represent one of combinations of amino acid residues crosslinked to each other by the thioether bond, and the amino acid residues described in the bold font which is not in the italic font represents one of combinations of amino acid residues crosslinked to each other by the thioether bond.

For example, in cyclic peptide 1, "Dap" in the italic font and "Hcy" in the italic font represent amino acid residues crosslinked by the thioether bond, and "I" in the bold font and "Hcy" in the bold font represent amino acid residues crosslinked by the thioether bond.

In the column of $X^a$ in Table 3-1 and Table 3-2, "α-$NH_2$" means that α-$NH_2$ of an amino acid residue forms a thioether bond with an amino acid residue, which is a bonding partner, through a chloroacetyl group (however, the chloro group is not present after the formation of thioether bond).

For example, in the cyclic peptide 21 where the amino acid residue $X^a$ is "K" (lysine), not $NH_2$ on the side chain but "α-$NH_2$" of lysine forms a thioether bond with an amino acid residue, which is a bonding partner, through a chloroacetyl group.

TABLE 3-1

| | Cyclic peptide | | | | | | | |
|---|---|---|---|---|---|---|---|---|
| | | Amino acid sequence | Crosslinking moiety amino acid residue 1 | | Crosslinking moiety amino acid residue 2 | | |
| Number | Identification name | (N terminal -> C terminal) | $X^a$ | $X^b$ | $X^c$ | $X^d$ | SEQ ID NO. |
| 1 | Cyclic peptide 1 | **I*(Dap(acetyl))***RGD-***(Hcy)***-F-**(Hcy)**-KKK | α-$NH_2$ | Hcy | Dap | Hcy | 1 |
| 2 | Cyclic peptide 2 | **I*(Dab(acetyl))***RGD-***(Hcy)***-F-**(Hcy)**-KKK | α-$NH_2$ | Hcy | Dab | Hcy | 2 |
| 3 | Cyclic peptide 3 | **I*(Orn(acetyl))***RGD-***(Hcy)***-F-**(Hcy)**-KKK | α-$NH_2$ | Hcy | Orn | Hcy | 3 |
| 4 | Cyclic peptide 4 | **I*(K(acetyl))***RGD-***(Hcy)***-F-**(Hcy)**-KKK | α-$NH_2$ | Hcy | K | Hcy | 4 |
| 5 | Cyclic peptide 5 | **I**-***(Hcy)***-RGD***(Dap(acetyl))***F-**(Hcy)**-KKK | α-$NH_2$ | Hcy | Hcy | Dap | 5 |
| 6 | Cyclic peptide 6 | **I*C***RGD***(Dap(acetyl))***F**C**KKK | α-$NH_2$ | C | C | Dap | 6 |
| 7 | Cyclic peptide 7 | **I**-***(Hcy)***-RGD***(Dab(acetyl))***F-**(Hcy)**-KKK | α-$NH_2$ | Hcy | Hcy | Dab | 7 |
| 8 | Cyclic peptide 8 | **I*C***RGD***(Dap(acetyl))***F**C**KKK | α-$NH_2$ | C | C | Dab | 8 |
| 9 | Cyclic peptide 9 | **I**-***(Hcy)***-RGD***(Orn(acetyl))***F-**(Hcy)**-KKK | α-$NH_2$ | Hcy | Hcy | Orn | 9 |
| 10 | Cyclic peptide 10 | **I*C***RGD***(Orn(acetyl))***F**C**KKK | α-$NH_2$ | C | C | Orn | 10 |
| 11 | Cyclic peptide 11 | **I**-***(Hcy)***-RGD***(K(acetyl))***F-**(Hcy)**-KKK | α-$NH_2$ | Hcy | Hcy | K | 11 |
| 12 | Cyclic peptide 12 | **I*C***RGD***(K(acetyl))***F**C**KKK | α-$NH_2$ | C | C | K | 12 |
| 13 | Cyclic peptide 13 | **I*(Dap(acetyl))***RGD-***(Hcy)***-F-**C**-KKK | α-$NH_2$ | C | Dap | Hcy | 13 |
| 14 | Cyclic peptide 14 | **I*(Dap(acetyl))***RGD-***C***-F-**(Hcy)**-KKK | α-$NH_2$ | Hcy | Dap | C | 14 |
| 15 | Cyclic peptide 15 | **I*(Orn(acetyl))***RGD-***(Hcy)***-F-**C**-KKK | α-$NH_2$ | C | Orn | Hcy | 15 |
| 16 | Cyclic peptide 16 | **I*(Orn(acetyl))***RGD-***C***-F-**(Hcy)**-KKK | α-$NH_2$ | Hcy | Orn | C | 16 |
| 17 | Cyclic peptide 17 | **I**-***(Hcy)***-RGD***(K(acetyl))***-F-**C**-KKK | α-$NH_2$ | C | Hcy | K | 17 |

TABLE 3-1-continued

| Number | Identification name | Cyclic peptide<br>Amino acid sequence<br>(N terminal -> C terminal) | Crosslinking moiety amino acid residue 1<br>$X^a$ | <br>$X^b$ | Crosslinking moiety amino acid residue 2<br>$X^c$ | <br>$X^d$ | SEQ ID NO. |
|---|---|---|---|---|---|---|---|
| 18 | Cyclic peptide 18 | I-C-RGD(K(acetyl))F-(Hcy)-KKK | α-$NH_2$ | Hcy | C | K | 18 |
| 19 | Cyclic peptide 19 | I-(Hcy)-RGD(Dab(acetyl))-F-C-KKK | α-$NH_2$ | C | Hcy | Dab | 19 |
| 20 | Cyclic peptide 20 | I-C-RGD(Dab(acetyl))F-(Hcy)-KKK | α-$NH_2$ | Hcy | C | Dab | 20 |
| 21 | Cyclic peptide 21 | K(Dab(acetyl))RGD-(Hcy)-F-(Hcy)-KKK | α-$NH_2$ | Hcy | Dap | Hcy | 21 |
| 22 | Cyclic peptide 22 | I-(Hcy)-RGD(K(acetyl))F-(Hcy)-K | α-$NH_2$ | Hcy | Hcy | K | 22 |
| 23 | Cyclic peptide 23 | I(Orn(acetyl))RGD-(Hcy)-F-(Pen)-KKK | α-$NH_2$ | Pen | Orn | Hcy | 23 |
| 24 | Cyclic peptide 24 | E(Orn(acetyl))RGD-(Hcy)-F-(Pen)-KKK | α-$NH_2$ | Pen | Orn | Hcy | 24 |

TABLE 3-2

| Number | Identification name | Cyclic peptide<br>Amino acid sequence<br>(N terminal -> C terminal) | Crosslinking moiety amino acid residue 1<br>$X^a$ | <br>$X^b$ | Crosslinking moiety amino acid residue 2<br>$X^c$ | <br>$X^d$ | SEQ ID NO. |
|---|---|---|---|---|---|---|---|
| 25 | Cyclic peptide 25 | Y-(Hcy)-RGD(K(acetyl))F-(Hcy)-KKK | α-$NH_2$ | Hcy | Hcy | K | 25 |
| 26 | Cyclic peptide 26 | L-(Hcy)-RGD(K(acetyl))F-(Hcy)-KKK | α-$NH_2$ | Hcy | Hcy | K | 26 |
| 27 | Cyclic peptide 27 | T-(Hcy)-RGD(K(acetyl))F-(Hcy)-KKK | α-$NH_2$ | Hcy | Hcy | K | 27 |
| 28 | Cyclic peptide 28 | V-(Hcy)-RGD(K(acetyl))F-(Hcy)-KKK | α-$NH_2$ | Hcy | Hcy | K | 28 |
| 29 | Cyclic peptide 29 | D-(Hcy)-RGD(K(acetyl))F-(Hcy)-KKK | α-$NH_2$ | Hcy | Hcy | K | 29 |
| 30 | Cyclic peptide 30 | E-(Hcy)-RGD(K(acetyl))F-(Hcy)-KKK | α-$NH_2$ | Hcy | Hcy | K | 30 |
| 31 | Cyclic peptide 31 | I-(Hcy)-RGD(K(acetyl))P-(Hcy)-KKK | α-$NH_2$ | Hcy | Hcy | K | 31 |
| 32 | Cyclic peptide 32 | I-(Hcy)-RGD(K(acetyl))Y-(Hcy)-KKK | α-$NH_2$ | Hcy | Hcy | K | 32 |
| 33 | Cyclic peptide 33 | I-(Hcy)-RGD(K(acetyl))FR-(Hcy)-KKK | α-$NH_2$ | Hcy | Hcy | K | 33 |
| 34 | Cyclic peptide 34 | I-(Hcy)-RGD(K(acetyl))FA-(Hcy)-KKK | α-$NH_2$ | Hcy | Hcy | K | 34 |
| 35 | Cyclic peptide 35 | I-(Hcy)-RGD(K(acetyl))F-(Hcy)-AKKK | α-$NH_2$ | Hcy | Hcy | K | 35 |
| 36 | Cyclic peptide 36 | A-(Hcy)-(Hcy)-RGD(K(acetyl))F(K(acetyl))KKK | Hcy | K | Hcy | K | 36 |
| 37 | Cyclic peptide 37 | KKK-(Hcy)-(Hcy)-RGD(K(acetyl))F(K(acetyl))A | Hcy | K | Hcy | K | 37 |
| 38 | Cyclic peptide 38 | V(Orn(acetyl))RGD-(Hcy)-F-(Hcy)-KKK | α-$NH_2$ | Hcy | Orn | Hcy | 38 |
| 39 | Cyclic peptide 39 | D(Orn(acetyl))RGD-(Hcy)-F-(Hcy)-KKK | α-$NH_2$ | Hcy | Orn | Hcy | 39 |
| 40 | Cyclic peptide 40 | E(Orn(acetyl))RGD-(Hcy)-F-(Hcy)-KKK | α-$NH_2$ | Hcy | Orn | Hcy | 40 |
| 41 | Cyclic peptide 41 | V-(Hcy)-RGD(Orn(acetyl))F-(Hcy)-KKK | α-$NH_2$ | Hcy | Hcy | Orn | 41 |
| 42 | Cyclic peptide 42 | D-(Hcy)-RGD(Orn(acetyl))F-(Hcy)-KKK | α-$NH_2$ | Hcy | Hcy | Orn | 42 |
| 43 | Cyclic peptide 43 | E-(Hcy)-RGD(Orn(acetyl))F-(Hcy)-KKK | α-$NH_2$ | Hcy | Hcy | Orn | 43 |
| 44 | Cyclic peptide 44 | V-(Hcy)-RGD(K(acetyl))F-(Hcy)-AKKK | α-$NH_2$ | Hcy | Hcy | K | 44 |
| 45 | Cyclic peptide 45 | D-(Hcy)-RGD(K(acetyl))F-(Hcy)-AKKK | α-$NH_2$ | Hcy | Hcy | K | 45 |

TABLE 3-2-continued

| | Cyclic peptide | | | | | | |
|---|---|---|---|---|---|---|---|
| | Identification | Amino acid sequence | Crosslinking moiety amino acid residue 1 | | Crosslinking moiety amino acid residue 2 | | SEQ ID |
| Number | name | (N terminal -> C terminal) | $X^a$ | $X^b$ | $X^c$ | $X^d$ | NO. |
| 46 | Cyclic peptide 46 | **E-*(Hcy)*-**RGD***(K(acetyl))***F-**(Hcy)**-AKKK | α-$NH_2$ | Hcy | Hcy | K | 46 |
| 47 | Cyclic peptide 47 | **E-*(Hcy)*-**RGD***(Orn(acetyl))***F-**(Hcy)**-AKKK | α-$NH_2$ | Hcy | Hcy | Orn | 47 |

Among these, the cyclic peptides 3, 11, 14 to 18, 20, 22 to 30, 35, 38 to 40, and 42 to 47 are preferable, and the cyclic peptides 11, 22, 25 to 30, 35, 38 to 40, and 42 to 47 are more preferable, and the cyclic peptides 29 and 30 are still more preferable.

The sequence variation may be applied by considering the entire cyclic peptide as a reference sequence. As a result, an amino acid sequence in which an amino acid residue is added, deleted, or substituted with respect to any one of the amino acid sequences of SEQ ID NO: 1 to SEQ ID NO: 47 is capable of being used as long as the requirements of the cyclic peptide according to the present disclosure are satisfied. However, the RGD region in the cyclic segment should not be modified. In a case of adding, deleting, or substituting an amino acid residue with respect to any one of the amino acid sequences of SEQ ID NO: 1 to SEQ ID NO: 47, the total number of amino acid residues added, deleted, or substituted is preferably 1 to 10, more preferably 1 to 5, still more preferably 1 to 3, and particularly preferably 1 or 2.

The cyclic peptide according to the present disclosure preferably has a sequence identity of 70% or more, more preferably has a sequence identity of 80% or more, and still more preferably has a sequence identity of 90%, with respect to any one of the amino acid sequences of SEQ ID NO: 1 to SEQ ID NO: 47. For example, the range of the amino acid sequence having a sequence identity of 70% or more with respect to the amino acid sequence of SEQ ID NO: 1 also includes the amino acid sequence of SEQ ID NO: 1 itself.

In the present disclosure, the sequence identity between two amino acid sequences is determined as follows.

(i) Two Amino Acid Sequences are Aligned

The alignment of the two sequences can be carried out using, for example, an alignment algorithm and/or a program, such as FASTA or BLAST that can be used by default settings.

(ii) A Sequence Identity is Calculated

Based on the obtained alignment, the sequence identity is calculated by the following expression.

The sequence identity [%]=(the number of matching positions/the total number of positions)×100[%]

The total number of positions is the length of the alignment, and the number of matching positions is the number of positions where the kinds of amino acids match.

(iii) Calculation Example of Sequence Identity

For example, the following amino acid sequences are assumed.

```
Sequence A
                         (SEQ ID NO: 51)
AYHRGELVWE

Sequence B
                         (SEQ ID NO: 52)
SAWHGELVW
```

In a case where these are aligned under the above conditions, the result becomes as follows. Here, a symbol "|" is assigned to a place where the kind of amino acid (residue) matches between the sequences A and B for visual convenience. In addition, "-" indicates a place where there is no corresponding amino acid.

```
Array A: -AYHRGELVWE (SEQ ID NO: 51)
            ||| |||||
Array B: SAWH-GELVW- (SEQ ID NO: 52)
```

In this example, the total number of positions is 11, and the number of matching positions is 7, and thus the sequence identity calculated according to the above expression is, 7/11× 100=63.6%.

(Cell Scaffold Material)

The cell scaffold material according to the present disclosure contains the cyclic peptide according to the present disclosure and a base material.

Cells are supported by an extracellular matrix in vivo, and thus in a case where the cyclic peptide according to the present disclosure is used as a cell scaffold material that reproduces the same state as above is used, it is possible to culture cells better.

Examples of the base material for cell culture include a matrix composed of biodegradable polyesters such as polylactic acid, polyglycolic acid, and polycaprolactone, collagen or gelatin which is a heat-denatured product of collagen, glycoproteins such as fibronectin, or polysaccharides such as hyaluronic acid, chitin, and alginic acid. For example, in a case where the immobilizing functional group in the cyclic peptide according to the present disclosure is reacted with a functional group in the base material, the cyclic peptide according to the present disclosure can be bound to the base material. For example, in a case where the cyclic peptide according to the present disclosure has an amino group of a lysine residue as the immobilizing functional group, the amino group is reacted with a carboxy group on the base material to form an amide bond, whereby the cyclic peptide can be immobilized to the base material. In a case of using such a method, it is possible to obtain a cell scaffold material in which the cyclic peptide according to the present disclosure is bound to the surface of the base material. The amount of the cyclic peptide according to the present disclosure is not particularly limited; however, it may be 0.01% by mass to 100% by mass and may be 0.1% by mass to 50% by mass with respect to the total mass of the base material.

The cell scaffold material according to the present disclosure can be applied onto any culture tool such as a petri dish, a flask, a plate (for example, a polystyrene well plate), a culture bag, a hollow fiber membrane, or beads.

Since the cell scaffold material according to the present disclosure contains the cyclic peptide according to the present disclosure, it has a good binding property to integrin, and thus cells can adhere well to the cell scaffold material.

The cell to be cultured is not particularly limited as long as it is a cell of an organism expressing integrin; however, it may be any animal cell, may be any vertebrate animal cell, may be any mammal cell, and may be a human cell or a non-human mammal cell.

Examples of the cell include an embryonic stem (ES) cell, an induced pluripotent stem (iPS) cell, a perinatal stem cell, an amniotic fluid-derived stem cell (AFSC), a mesenchymal stem cell (MSC) of any origin, any tissue-type progenitor cell or adult cell of which the differentiation direction has been determined, a mature cell, a normal cell, an affected cell, and a tumor cell. More specific examples thereof include a liver cell, a parenchymal cell, a stellate cell, an endothelial cell, a hepatocyte, a bile duct cell, a biliary tree cell, and a pancreatic cell. Examples of these cells are also applied to the cell separating material and the medium described later.

(Cell Separating Material)

The cell separating material according to the present disclosure contains the cyclic peptide according to the present disclosure and a holding material. Since the cell separating material according to the present disclosure contains the cyclic peptide according to the present disclosure, it can bind to the integrin on the cell surface and capture cells. As a result, in a case where the cell separating material according to the present disclosure is used, for example, in affinity chromatography; cells can be efficiently separated from the cell suspension.

For example, in a case where an immobilizing functional group in the cyclic peptide according to the present disclosure is reacted with a functional group in the holding material, the cyclic peptide according to the present disclosure can be bound to the holding material. For example, in a case where the cyclic peptide according to the present disclosure has an amino group of a lysine residue as the immobilizing functional group, the amino group is reacted with a carboxy group on the holding material to form an amide bond, whereby the cyclic peptide can be immobilized to the holding material.

The holding material is not particularly limited and may be composed of a material selected from, for example, polysaccharides such as agarose, dextran, starch, cellulose, pullulan, chitin, chitosan, cellulose triacetate, and cellulose diacetate, and derivatives thereof, and vinyl-based polymers such polyacrylamide, polymethacrylamide, polyacrylate, polymethacrylate, polyalkyl vinyl ether, and polyvinyl alcohol.

These materials may form a crosslinking structure. The crosslinking structure tends to improve mechanical strength.

The holding material is preferably composed of one or two or more of the above materials.

In addition, the holding material is preferably porous, more preferably a porous membrane or porous particles, and still more preferably porous particles.

A cell separating material in which the cyclic peptide according to the present disclosure is immobilized to a water-insoluble holding material can also be used in affinity chromatography.

Examples of the water-insoluble holding material include polysaccharides such as crystalline cellulose, crosslinked cellulose, crosslinked agarose, crosslinked dextran, and crosslinked pullulan, organic holding materials such as an acrylate-based polymer, and a styrene-based polymer, inorganic holding material such as a glass bead and silica gel, and composite holding materials obtained by combining these, such as an organic-organic type and an organic-inorganic type.

The water-insoluble holding material is more preferably polysaccharides or an acrylate-based polymer and still more preferably polysaccharides such as agarose and cellulose from the viewpoint of alkali resistance.

Examples of the commercially available product that can be used as a water-insoluble holding material include Cellufine (CELLUFINE is a registered trade name) GCL2000 (manufactured by JNC Corporation) and Cellufine MAX (manufactured by JNC Corporation), which are porous cellulose gels: Sephacryl (SEPHACRYL is a registered trade name) S-1000 SF (manufactured by GE Healthcare) in which allyl dextran and methylenebisacrylamide are covalently crosslinked: TOYOPEARL (TOYOPEARL is a registered trade name) (manufactured by Tosoh Corporation), TOYOPEARL AF-Carboxy-650 (manufactured by Tosoh Corporation), and TOYOPEARL GigaCap CM-650 (manufactured by Tosoh Corporation), which is an acrylate-based holding material: Sepharose (SEPHAROSE is a registered trade name) CL4B (manufactured by GE Healthcare), which is agarose-based crosslinked holding material; and Eupergit (EUPERGIT is a registered trade name) C250L (manufactured by Sigma-Aldrich Co., LLC), which is a polymethacrylamide activated with an epoxy group.

However, the water-insoluble holding material in the present disclosure is not limited to these holding materials or activated holding materials. In addition, the water-insoluble holding material that is used in the present disclosure preferably has a large surface area and is preferably a porous material having a large number of pores of a proper size in consideration of the using purpose and the using method of the present adsorbing material. The form of the holding material is not particularly limited. Any form such as a bead shape, a fibrous shape, a membrane shape, or a hollow yarn shape, is possible, and any form can be selected.

Examples of the method of immobilizing the cyclic peptide according to the present disclosure to a water-insoluble holding material include, which are not limited to, an immobilization method using an amino group of a lysine residue as described above.

It is possible to adopt a method generally adopted in a case of immobilizing a protein or a polypeptide to a holding material. Examples thereof include a method in which a holding material is reacted with cyanogen bromide, epichlorohydrin, diglycidyl ether, tosyl chloride, tresyl chloride, hydrazine, or the like to activate the holding material or introduce a reactive functional group on the surface of the holding material and a reaction with the cyclic peptide according to the present disclosure is carried out for immobilization and an immobilization method in which a condensing reagent such as carbodiimide or a reagent having a plurality of functional groups in the molecule, such as glyceraldehyde, is added to a system in which a holding material and the cyclic peptide according to the present disclosure are present to carry out condensation and cross-linking.

In a case of immobilizing the cyclic peptide according to the present disclosure to a holding material, it is preferable to dissolve (disperse) the cyclic peptide according to the present disclosure in an aqueous solvent (an aqueous dispersion medium) or an organic solvent (an organic dispersion medium).

The aqueous solvent (the aqueous dispersion medium) is not particularly limited; however, examples thereof include a 4-(2-hydroxyethyl)-1-piperazineethanesulfonic acid (HEPES) buffer solution, an acetate buffer solution, a phosphate buffer solution, a citrate buffer solution, and a Tris-hydrochloride buffer solution.

The organic solvent (the organic dispersion medium) is not particularly limited; however, a polar organic solvent is preferable, and dimethyl sulfoxide (DMSO), N,N-dimethylformamide (DMF), or alcohol is particularly preferable. Examples thereof include methanol, ethanol, isopropyl alcohol (IPA), 2,2,2-trifluoroethanol (TFE), and 1,1,1,3,3,3-hexafluoro-2-propanol (HFIP).

The pH condition for immobilizing the cyclic peptide according to the present disclosure is not particularly limited, and may be any condition of acidic, neutral, or alkaline condition, and may be appropriately set according to, for example, the solvent (the dispersion medium) to be used.

For example, in the case of making it alkaline, a base such as diazabicycloundecene (DBU) or triethylamine (TEA) may be added to dimethyl sulfoxide (DMSO) or alcohol.

In a case where the above cell separating material is used as a packing material for affinity chromatography, the density of the cyclic peptide according to the present disclosure is not particularly limited; however, it may be preferably 0.1 mmol/packing material 1 L to 1,000 mmol/packing material 1 L, more preferably 0.1 mmol/packing material 1 L to 100 mmol/packing material 1 L, and still more preferably 0.5 mmol/packing material 1 L to 20 mmol/packing material 1 L. In a case where the density of the cyclic peptide is within the above range, the using amount of the cyclic peptide according to the present disclosure is well balanced with the cell separation performance, and cells can be separated efficiently at a lower cost.

The cell that is separated by the cell separating material according to the present disclosure is not particularly limited as long as it is a cell of an organism expressing integrin; however, it may be any animal cell, may be any vertebrate animal cell, may be any mammal cell, and may be a human cell or a non-human mammal cell.

(Medium)

The medium according to the present disclosure contains the cyclic peptide according to the present disclosure and a culture component.

In a case where the cyclic peptide according to the present disclosure is contained in the medium according to the present disclosure, the binding of the integrin of the cell cultured in the medium to the cyclic peptide occurs, which provides an effect such as an increase in cell viability through the apoptosis suppression due to signal transduction from the integrin.

The above culture component refers to a medium component for culturing cells. In addition, the cell to be cultured is not particularly limited as long as it is a cell of an organism expressing integrin; however, it may be any animal cell, may be any vertebrate animal cell, may be any mammal cell, and may be a human cell or a non-human mammal cell.

The medium containing a culture component may be appropriately selected according to the kind of cells to be cultured. Examples thereof include Dulbecco modified Eagle's medium (DMEM), Eagle's minimum essential medium (MEM), F12, Ham, RPMI 1640, MCDB (MCDB 102, 104, 107, 131, 153, 199, or the like), L15, SkBM (registered trade name), RITC80-7, and MesenPro (Thermo Fisher Scientific, Inc.).

As the culture component, a medium such as the above-described medium may be used as it is in the state of the standard composition (for example, as it is in the state of having been sold), or the composition may be appropriately changed according to the cell kind or the cell conditions. Accordingly; the culture component is not limited to the one having a known composition, and one or two or more components may be added, removed, increased, or decreased.

The amino acids to be contained in the culture component is not particularly limited, and examples thereof include known amino acids to be contained in the culture component. Examples thereof include L-arginine, L-cystine, L-glutamine, glycine, L-histidine, L-isoleucine, L-leucine, L-lysine, L-methionine, L-phenylalanine, L-serine, L-threonine, L-tryptophan, L-tyrosine, and L-valine.

The vitamins to be contained in the culture component is not particularly limited; however, examples thereof include calcium D-pantothenate, choline chloride, folic acid, isoinositol, niacinamide, riboflavin, thiamine, pyridoxine, biotin, lipoic acid, vitamin B12, adenine, and thymidine.

The electrolyte to be contained in the culture component is not particularly limited, and examples thereof include a known electrolyte to be contained in the culture component. Examples of the electrolyte include $CaCl_2$), KCl, $MgSO_4$, NaCl, $NaH_2PO_4$, $NaHCO_3$, $Fe(NO_3)_3$, $FeSO_4$, $CuSO_4$, $MnSO_4$, $Na_2SiO_3$, $(NH_4)_6Mo_7O_{24}$, $NaVO_3$, $NiCl_2$, and $ZnSO_4$.

In addition to these components, the culture component may contain sugars such as D-glucose, sodium pyruvate, a pH indicator such as phenol red, putrescine, and antibiotics.

The culture component may contain or may not contain serum. The content of serum in the medium according to the present disclosure is preferably 0% by volume or more and 30% by volume or less, more preferably 0% by volume or more and 10% by volume or less, still more preferably 0% by volume or more and 5% by volume or less, and particularly preferably 0% by volume or more and 2% by volume or less.

The content of the cyclic peptide according to the present disclosure in the medium according to the present disclosure is not particularly limited; however, it is, for example, 0.01 ng/mL to 10 mg/mL and may be 0.1 ng/mL to 1 mg/mL. In the medium according to the present disclosure, unlike the case of the cell scaffold material or the cell separating material, it is not particularly necessary to immobilize the cyclic peptide.

As described above, according to the present disclosure, it is possible to provide a cyclic peptide excellent in integrin binding property and excellent in molecule stability, for example, excellent in the alkali resistance, and a cell scaffold material, a cell separating material, and a medium, which contain the cyclic peptide.

EXAMPLES

The embodiments according to the present disclosure will be described in more detail with reference to Examples below; however, the embodiments are not limited thereto.

In Examples, "M" means "mol/L".

(1) Synthesis of Cyclic Peptide

Each of the cyclic peptides 1 to 47 shown in Table 3-1 and Table 3-2 and the cyclic peptides 48 and 49 shown in Table 4 below was synthesized by using a fully automated peptide synthesizer (model number: PSSM-8, manufactured by Shimadzu Corporation). In a case where optical isomers are present in amino acid residues contained in the cyclic peptide prepared in Examples, all the amino acid residues are L-form isomers.

For example, the notation D in the peptide prepared in Example represents an L-aspartic acid residue.

TABLE 4

| | | Cyclic peptide | | | | | | |
|---|---|---|---|---|---|---|---|---|
| | | | Amino acid sequence | Crosslinking moiety amino acid residue 1 | | Crosslinking moiety amino acid residue 2 | | SEQ ID |
| | | Identification name | (N terminal -> C terminal) | $X^a$ | $X^b$ | $X^c$ | $X^d$ | NO. |
| Comparative | 1 | Cyclic peptide 48 | **K*****C***RGD***C***F**C**KKK | α-$NH_2$ | C | C | C | 48 |
| Example | 2 | Cyclic peptide 49 | A**C**D***C***RGD***C***F**C**GKKK | C | C | C | C | 49 |

In Table 4, in the cyclic peptide 48, "C" and "C" in the italic font indicate amino acid residues crosslinked by the disulfide bond, and "K" and "C" in the bold font indicate amino acid residues crosslinked by the thioether bond. In addition, in the cyclic peptide 49, "C's" in the italic font and "C's" in the bold font respectively indicate amino acid residues crosslinked by the disulfide bonds.

(2) Immobilization of Cyclic Peptide

A commercially available CM5 sensor chip (a carboxymethyl dextran introduction type, manufactured by GE Healthcare) was set in a surface plasmon resonance apparatus (product name: Biacore 3000, manufactured by GE Healthcare), the sensor was stabilized at a flow rate of 10 μL/min of a 4-(2-hydroxyethyl)-1-piperazineethanesulfonic acid (HEPES) buffer solution (20 mM HEPES-HCl, 150 mM NaCl, pH 7.4) for surface plasmon resonance (SPR), and 70 μL of a mixed aqueous solution of 0.2 M 1-(3-dimethylaminopropyl)-3-ethylcarbodiimide (EDC) and 0.04 M N-hydroxysuccinimide (NHS) was added thereto. Then, 300 μL of the sample solution of each of the above cyclic peptides diluted to 0.2 g/L with the HEPES buffer solution was supplied to the sensor chip, blocking treatment was subsequently carried out with an ethanolamine solution, and washing was carried out with a sodium hydroxide aqueous solution, whereby immobilization was carried out. However, only for the cyclic peptide 22, in which the number of lysine residues having an amino group as the immobilizing functional group was 1, the sample solution to be supplied to the sensor chip was set to 5,000 μL instead of 300 μL. Similarly; 70 μL of the mixed aqueous solution of 0.2 M EDC and 0.04 M NHS was added to another flow channel of the same sensor chip without immobilizing the sample, and then blocking treatment and washing treatment were carried out. Hereinafter, the obtained immobilization-treated sensor chip is referred to as an "immobilization-treated sensor chip A".

(3) Evaluation of Integrin Binding Property

After adding human integrin αvβ5 for 10 minutes at 25° C., which was diluted to 30 nM using a HEPES buffer solution to which magnesium chloride was added to 5 mM, in each flow channel of the immobilization-treated sensor chip A prepared in (1) above, the same HEPES buffer solution (containing 5 mM magnesium chloride) was allowed to flow as a running buffer for 30 minutes, and measurement was carried out with Biacore 3000.

Then, a regeneration treatment of removing human integrin αvβ5 was carried out by allowing a 0.5 M EDTA aqueous solution to flow through each flow channel for 10 minutes. Further, the above-described measurement process consisting of adding integrin for 10 minutes, allowing a running buffer to flow for 30 minutes, carrying out measurement with Biacore 3000, and carrying out regeneration treatment with 0.5 M EDTA aqueous solution was carried out in the same manner for 100 nM human integrin αvβ5, 300 nM human integrin αvβ5, and 1,000 nM human integrin αvβ5. Dissociation constant between the cyclic peptide and human integrin αvβ5 was calculated from the difference between the value measured by Biacore 3000 in the flow channel immobilized with the cyclic peptide and the value measured by Biacore 3000 in the flow channel unimmobilized with the cyclic peptide, in a case where each concentration of human integrin αvβ5 was allowed to flow; and the integrin binding property was evaluated according to the following evaluation standards. It is preferable that the evaluation result satisfies the evaluation standard A, B, or C. The evaluation results are shown in Table 5-1 and Table 5-2.

In a case where the cyclic peptides of evaluation standards A, B, and C are used, the specific binding between the cyclic peptide and integrin is possible, and thus more efficient cell control is possible.

(Evaluation Standards for Dissociation Constant)

A . . . The dissociation constant is 50 nM or less.

B . . . The dissociation constant is more than 50 nM and 100 nM or less.

C . . . The dissociation constant is more than 100 nM and 200 nM or less.

D . . . The dissociation constant is more than 200 nM.

(4) Evaluation of Molecule Stability

The molecule stability of the cyclic peptide was evaluated by analyzing the alkali-treated cyclic peptide aqueous solution by liquid chromatography mass spectroscopy (LC/MS).

The alkali treatment was carried out by the following method. A 500 μM cyclic peptide aqueous solution was prepared, an equivalent of 1 M sodium hydroxide aqueous solution was added to this aqueous solution, and the resultant mixture was incubated at 15° C. for 20 minutes to obtain an alkali-treated cyclic peptide aqueous solution. The cyclic peptide residual rate was calculated by setting the total area of all peaks of the cyclic peptide before alkali treatment in LC/MS to 100% and determining the proportion of the total area of all peaks in LC/MS of the alkali-treated cyclic peptide aqueous solution, and the molecule stability was evaluated according to the following evaluation standards. It is preferable that the evaluation result satisfies the evaluation standard A, B, or C.

The evaluation results are shown in Table 5-1 and Table 5-2.

In a case where the cyclic peptides of the evaluation standards A, B, and C are used, the cyclic peptide can be specifically bound to cells even in a case of being used for a long period of time or repeatedly, cell control is possible even in a case of being used in a long-term or repeated process, and thus the cost can be further reduced.

(Evaluation Standards for Cyclic Peptide Residual Rate)

A . . . The residual rate of the cyclic peptide is 70% or more.

B . . . The residual rate of the cyclic peptide is 50% or more and less than 70%.

C . . . The residual rate of the cyclic peptide is 30% or more and less than 50%.

D . . . The residual rate of the cyclic peptide is less than 30%.

The conditions of the LC/MS used for the evaluation of molecule stability were set as follows.

LC apparatus: Prominence series (pump, column oven, autosampler, detector) (manufactured by Shimadzu Corporation)

MS detector: LC/MS2010EV (manufactured by Shimadzu Corporation)

Column: Cadenza CD-C18, inner diameter 2.0 mm×length 250 mm, particle size: 3 μm (manufactured by Imtakt Corporation)

Eluent A: a solution (pH 3) containing 10 mM ammonium formate as a solute, where the solvent is 100% water.

Eluent B: a solution (pH 3) containing 10 mM ammonium formate as a solute, where the solvent is acetonitrile/water=90/10.

Flow rate: 0.2 mL/min

Injection volume: 4 μL

Gradient: 0% to 30%: Eluent B (0 to 30 minutes), 100%: Eluent B (30 to 40 minutes), 0%: Eluent B (40 to 60 minutes)(B indicates the eluent B)

Column temperature: 45° C.

Ionization method: electrospray ionization (ESI) positive, ESI negative

TABLE 5-1

| | Cyclic peptide | | | | | | | | Performance evaluation | | |
|---|---|---|---|---|---|---|---|---|---|---|---|
| | | | Crosslinking moiety amino acid residue 1 | | Crosslinking moiety amino acid residue 2 | | | | | | |
| Example | Identification name | Amino acid sequence (N terminal ->C terminal) | $X^a$ | $X^b$ | $X^c$ | $X^d$ | Crosslinking structure | | Integrin binding property | Molecule stability | SEQ ID NO. |
| 1 | Cyclic peptide 1 | I(Dap(acetyl))RGD-(Hcy)-F-(Hcy)-KKK | α-$NH_2$ | Hcy | Dap | Hcy | Thioether bond | | B | A | 1 |
| 2 | Cyclic peptide 2 | I(Dab(acetyl))RGD-(Hcy)-F-(Hcy)-KKK | α-$NH_2$ | Hcy | Dab | Hcy | Thioether bond | | C | A | 2 |
| 3 | Cyclic peptide 3 | I(Orn(acetyl))RGD-(Hcy)-F-(Hcy)-KKK | α-$NH_2$ | Hcy | Orn | Hcy | Thioether bond | | A | A | 3 |
| 4 | Cyclic peptide 4 | I(K(acetyl))RGD-(Hcy)-F-(Hcy)-KKK | α-$NH_2$ | Hcy | K | Hcy | Thioether bond | | B | A | 4 |
| 5 | Cyclic peptide 5 | I-(Hcy)-RGD(Dap(acetyl))F-(Hcy)-KKK | α-$NH_2$ | Hcy | Hcy | Dap | Thioether bond | | B | A | 5 |
| 6 | Cyclic peptide 6 | ICRGD(Dap(acetyl))FCKKK | α-$NH_2$ | C | C | Dap | Thioether bond | | C | B | 6 |
| 7 | Cyclic peptide 7 | I-(Hcy)-RGD(Dab(acetyl))F-(Hcy)-KKK | α-$NH_2$ | Hcy | Hcy | Dab | Thioether bond | | B | A | 7 |
| 8 | Cyclic peptide 8 | ICRGD(Dab(acetyl))FCKKK | α-$NH_2$ | C | C | Dab | Thioether bond | | A | B | 8 |
| 9 | Cyclic peptide 9 | I-(Hcy)-RGD(Orn(acetyl))F-(Hcy)-KKK | α-$NH_2$ | Hcy | Hcy | Orn | Thioether bond | | B | A | 9 |
| 10 | Cyclic peptide 10 | ICRGD(Orn(acetyl))FCKKK | a-$NH_2$ | C | C | Orn | Thioether bond | | B | B | 10 |
| 11 | Cyclic peptide 11 | I-(Hcy)-RGD(K(acetyl))F-(Hcy)-KKK | α-$NH_2$ | Hcy | Hcy | K | Thioether bond | | A | A | 11 |
| 12 | Cyclic peptide 12 | ICRGD(K(acetyl))FCKKK | α-$NH_2$ | C | C | K | Thioether bond | | A | B | 12 |
| 13 | Cyclic peptide 13 | I(Dap(acetyl))RGD-(Hcy)-F-C-KKK | α-$NH_2$ | C | Dap | Hcy | Thioether bond | | B | A | 13 |
| 14 | Cyclic peptide 14 | I(Dap(acetyl))RGD-C-F-(Hcy)-KKK | α-$NH_2$ | Hcy | Dap | C | Thioether bond | | A | A | 14 |
| 15 | Cyclic peptide 15 | I(Orn(acetyl))RGD-(Hcy)-F-C-KKK | α-$NH_2$ | C | Orn | Hcy | Thioether bond | | A | A | 15 |
| 16 | Cyclic peptide 16 | I(Orn(acetyl))RGD-C-F-(Hcy)-KKK | α-$NH_2$ | Hcy | Om | C | Thioether bond | | A | A | 16 |
| 17 | Cyclic peptide 17 | I-(Hcy)-RGD(K(acetyl))F-C-KKK | α-$NH_2$ | C | Hcy | K | Thioether bond | | A | A | 17 |
| 18 | Cyclic peptide 18 | I-C-RGD(K(acetyl))F-(Hcy)-KKK | α-$NH_2$ | Hcy | C | K | Thioether bond | | A | A | 18 |
| 19 | Cyclic peptide 19 | I-(Hcy)-RGD(Dab(acetyl))F-C-KKK | α-$NH_2$ | C | Hcy | Dab | Thioether bond | | B | A | 19 |
| 20 | Cyclic peptide 20 | I-C-RGD(Dab(acetyl))F-(Hcy)-KKK | α-$NH_2$ | Hcy | C | Dab | Thioether bond | | A | A | 20 |

TABLE 5-1-continued

| | Cyclic peptide | | | | | | | Performance evaluation | | |
|---|---|---|---|---|---|---|---|---|---|---|
| | | | Crosslinking moiety amino acid residue 1 | | Crosslinking moiety amino acid residue 2 | | | | | |
| | Identification name | Amino acid sequence (N terminal ->C terminal) | $X^a$ | $X^b$ | $X^c$ | $X^d$ | Crosslinking structure | Integrin binding property | Molecule stability | SEQ ID NO. |
| 21 | Cyclic peptide 21 | **K*(Dap(acetyl))***RGD-**(Hcy)**-F-**(Hcy)**-KKK | $\alpha$-$NH_2$ | Hcy | Dap | Hcy | Thioether bond | B | A | 21 |
| 22 | Cyclic peptide 22 | **I-*(Hcy)***-RGD***(K(acetyl))***F-**(Hcy)**-K | $\alpha$-$NH_2$ | Hcy | Hcy | K | Thioether bond | A | A | 22 |
| 23 | Cyclic peptide 23 | **I*(Orn(acetyl))***RGD-***(Hcy)***-F-**(Pen)**-KKK | $\alpha$-$NH_2$ | Pen | Orn | Hcy | Thioether bond | A | A | 23 |
| 24 | Cyclic peptide 24 | **E*(Orn(acetyl))***RGD-***(Hcy)***-F-**(Pen)**-KKK | $\alpha$-$NH_2$ | Pen | Orn | Hcy | Thioether bond | A | A | 24 |

TABLE 5-2

| | | Cyclic peptide | | | | | | | | | |
|---|---|---|---|---|---|---|---|---|---|---|---|
| | | Identification name | Amino acid sequence (N terminal -> C terminal) | Crosslinking moiety amino acid residue 1 $X^a$ | $X^b$ | Crosslinking moiety amino acid residue 2 $X^c$ | $X^d$ | Crosslinking structure | Performance evaluation Integrin binding property | Molecule stability | SEQ ID NO. |
| Example | 25 | Cyclic peptide 25 | Y-(Hcy)-RGD(K(acetyl))F-(Hcy)-KKK | α-$NH_2$ | Hcy | Hcy | K | Thioether bond | A | A | 25 |
| | 26 | Cyclic peptide 26 | L-(Hcy)-RGD(K(acetyl))F-(Hcy)-KKK | α-$NH_2$ | Hcy | Hcy | K | Thioether bond | A | A | 26 |
| | 27 | Cyclic peptide 27 | T-(Hcy)-RGD(K(acetyl))F-(Hcy)-KKK | a-$NH_2$ | Hcy | Hcy | K | Thioether bond | A | A | 27 |
| | 28 | Cyclic peptide 28 | V-(Hcy)-RGD(K(acetyl))F-(Hcy)-KKK | α-$NH_2$ | Hcy | Hcy | K | Thioether bond | A | A | 28 |
| | 29 | Cyclic peptide 29 | D-(Hcy)-RGD(K(acetyl))F-(Hcy)-KKK | α-$NH_2$ | Hcy | Hcy | K | Thioether bond | A | A | 29 |
| | 30 | Cyclic peptide 30 | E-(Hcy)-RGD(K(acetyl))F-(Hcy)-KKK | α-$NH_2$ | Hcy | Hcy | K | Thioether bond | A | A | 30 |
| | 31 | Cyclic peptide 31 | I-(Hcy)-RGD(K(acetyl))P-(Hcy)-KKK | α-$NH_2$ | Hcy | Hcy | K | Thioether bond | B | A | 31 |
| | 32 | Cyclic peptide 32 | I-(Hcy)-RGD(K(acetyl))Y-(Hcy)-KKK | α-$NH_2$ | Hcy | Hcy | K | Thioether bond | B | A | 32 |
| | 33 | Cyclic peptide 33 | I-(Hcy)-RGD(K(acetyl))FR-(Hcy)-KKK | α-$NH_2$ | Hcy | Hcy | K | Thioether bond | C | A | 33 |
| | 34 | Cyclic peptide 34 | I-(Hcy)-RGD(K(acetyl))FA-(Hcy)-KKK | α-$NH_2$ | Hcy | Hcy | K | Thioether bond | B | A | 34 |
| | 35 | Cyclic peptide 35 | I-(Hcy)-RGD(K(acetyl))F-(Hcy)-AKKK | α-$NH_2$ | Hcy | Hcy | K | Thioether bond | A | A | 35 |
| | 36 | Cyclic peptide 36 | A-(Hcy)-(Hcy)-RGD(K(acetyl))F(K(acetyl))KKK | Hcy | K | Hcy | K | Thioether bond | B | A | 36 |
| | 37 | Cyclic peptide 37 | KKK-(Hcy)-(Hcy)-RGD(K(acetyl))F(K(acetyl))A | Hcy | K | Hcy | K | Thioether bond | B | A | 37 |
| | 38 | Cyclic peptide 38 | V(Orn(acetyl))RGD-(Hcy)-F-(Hcy)-KKK | α-$NH_2$ | Hcy | Orn | Hcy | Thioether bond | A | A | 38 |
| | 39 | Cyclic peptide 39 | D(Orn(acetyl))RGD-(Hcy)-F-(Hcy)-KKK | α-$NH_2$ | Hcy | Orn | Hcy | Thioether bond | A | A | 39 |
| | 40 | Cyclic peptide 40 | E(Orn(acetyl))RGD-(Hcy)-F-(Hcy)-KKK | α-$NH_2$ | Hcy | Orn | Hcy | Thioether bond | A | A | 40 |
| | 41 | Cyclic peptide 41 | V-(Hcy)-RGD(Orn(acetyl))F-(Hcy)-KKK | α-$NH_2$ | Hcy | Hcy | Orn | Thioether bond | B | A | 41 |
| | 42 | Cyclic peptide 42 | D-(Hcy)-RGD(Orn(acetyl))F-(Hcy)-KKK | α-$NH_2$ | Hcy | Hcy | Orn | Thioether bond | A | A | 42 |
| | 43 | Cyclic peptide 43 | E-(Hcy)-RGD(Orn(acetyl))F-(Hcy)-KKK | α-$NH_2$ | Hcy | Hcy | Orn | Thioether bond | A | A | 43 |
| | 44 | Cyclic peptide 44 | V-(Hcy)-RGD(K(acetyl))F-(Hcy)-AKKK | α-$NH_2$ | Hcy | Hcy | K | Thioether bond | A | A | 44 |
| | 45 | Cyclic peptide 45 | D-(Hcy)-RGD(K(acetyl))F-(Hcy)-AKKK | α-$NH_2$ | Hcy | Hcy | K | Thioether bond | A | A | 45 |

TABLE 5-2-continued

| | | Cyclic peptide | | | | | | | Performance evaluation | | |
|---|---|---|---|---|---|---|---|---|---|---|---|
| | | | | Crosslinking moiety amino acid residue 1 | | Crosslinking moiety amino acid residue 2 | | | | | |
| | | Identification name | Amino acid sequence (N terminal -> C terminal) | $X^a$ | $X^b$ | $X^c$ | $X^d$ | Crosslinking structure | Integrin binding property | Molecule stability | SEQ ID NO. |
| | 46 | Cyclic peptide 46 | **E-*(Hcy)***-RGD***(K(acetyl))***F-**(Hcy)**-AKKK | $\alpha$-$NH_2$ | Hcy | Hcy | K | Thioether bond | A | A | 46 |
| | 47 | Cyclic peptide 47 | **E-*(Hcy)***-RGD***(Orn(acetyl))***F-**(Hcy)**-AKKK | $\alpha$-$NH_2$ | Hcy | Hcy | Orn | Thioether bond | A | A | 47 |
| Comparative Example | 1 | Cyclic peptide 48 | **K**CRGDCFCKKK | $\alpha$-$NH_2$ | C | C | C | Disulfide bond, thioether bond | A | D | 48 |
| | 2 | Cyclic peptide 49 | ACDCRGDCFCGKKK | C | C | C | C | Disulfide bond | A | D | 49 |

From the results shown in Table 5-1 and Table 5-2, it can be seen that the cyclic peptide according to the present disclosure is excellent in molecule stability as compared with the cyclic peptide of Comparative Example. In all Examples, the value of the residual rate of the cyclic peptide was 50% or more (the evaluation B or better), whereas in all Comparative Examples, the value of the residual rate of the cyclic peptide was 25% or less as the actual value. From the above, it can be seen that the cyclic peptide according to the present disclosure is excellent in both integrin binding property and molecule stability.

Next, using the cyclic peptide obtained as above, the cell scaffold material according to the present disclosure was prepared, and an iPS cell culture experiment was carried out using this cell scaffold material.

(Surface Treatment of Polystyrene Plate)

Using a plasma treating device (SCB-106 manufactured by SAKIGAKE-Semiconductor Co., Ltd.), a polystyrene 6-well plate (manufactured by Corning Incorporated) was subjected to surface treatment in an ammonia gas under the conditions of a gas pressure of 10 Pa, an output of 700 W, and a treatment time of 5 minutes.

(Preparation of CMD Coating Well)

9.5 g of distilled water was added to 0.5 g of sodium carboxymethyl dextran (manufactured by Meito Sangyo Co., Ltd., trade name: "CMD", molecular weight: 1 million, hereinafter may be also referred to as "CMD") and stirred to be sufficiently dissolved, whereby a 5% by weight CMD solution was prepared.

Next, 1 mL of distilled water was added to 383.4 mg of 1-ethyl-3-(3-dimethylaminopropyl) carbodiimide hydrochloride (hereinafter, may be also referred to as "EDC") (manufactured by Nacalai Tesque, Inc.) to prepare an EDC solution. Next, 1 mL of distilled water was added to 57.5 mg of N-hydroxysuccinimide (hereinafter, may be referred to as "NHS")(manufactured by FUJIFILM Wako Pure Chemical Corporation) to prepare an NHS Solution Next, 0.05 mL of the EDC solution and 0.05 mL of the NHS solution were added to 10 g of the CMD solution prepared above and stirred, and 1 mL of the obtained CMD-containing coating solution was immediately added dropwise to each of wells of the polystyrene plate subjected to surface treatment as described above. After allowing the polystyrene plate to stand at room temperature for 1 hour, the well was sufficiently washed with distilled water to remove the CMD-containing coating solution, whereby a CMD coating well was prepared.

(Preparation of Ligand Coating Well)

1 mL of an HBS-N buffer (manufactured by GE Healthcare Japan Corporation) was added to 0.2 mg of the cyclic peptide 11 to prepare a cyclic peptide solution. Next, 1 mL of distilled water was added to 76.7 mg of EDC to prepare an EDC solution. Next, 1 mL of distilled water was added to 11.5 mg of NHS to prepare an NHS solution. Next, 1 mL of distilled water was added to 1 mL of ethanolamine (manufactured by Bio-Rad Laboratories, Inc., trade name: "ProteOn ethanolamine HCL") to prepare an ethanolamine solution.

Next, 0.5 mL of the NHS solution was added to 0.5 mL of the EDC solution prepared above and stirred, and 1 mL of the obtained mixed solution was immediately added dropwise to the CMD coating well. After allowing the polystyrene plate to stand for 7 minutes, the well was sufficiently washed with distilled water to remove the mixed solution. Further, 1 mL of the cyclic peptide 11 solution was added dropwise to the well, and the well was allowed to stand for 60 minutes and then washed sufficiently with distilled water to remove the cyclic peptide solution. Further, 1 mL of the ethanolamine solution was added dropwise to the well, and after allowing to stand for 7 minutes, the well was sufficiently washed with distilled water to remove the ethanolamine solution to obtain a well (hereinafter referred to as a "ligand coating well") having a cell scaffold material, on which the cyclic peptide 11 was immobilized on CMD as a base material.

(γ Ray Sterilization Treatment)

The ligand coating well prepared as described above was sealed in a sterilization bag and subjected to γ ray sterilization treatment in an irradiation facility No. 1 manufactured by RADIA INDUSTRY Co., Ltd. under the condition of a dose of 25 kGy.

As a result of the above, a "γ ray irradiated cell scaffold material A" was prepared.

—Evaluation of iPS Cell Culture Performance of Peptide—

As the iPS cell, a 01434 clone established by Fujifilm Cellular Dynamics Inc. was used. The iPS cell was seeded in a culture polystyrene plate having the γ ray irradiated cell scaffold material A on the surface at a split rate=1:6, cultured for three days in a feeder-free ES and iPS cell culture medium (Stem Cell Technologies, product name: mTeSR1), and then the iPS cells were stripped to single cells and collected by treatment using a cell dissociation reagent (manufactured by Thermo Fisher Scientific, Inc., product name: TrypLE Select). From the obtained cell suspension, the number of cells was measured using a cell viability autoanalyzer (manufactured by Beckman Coulter Inc., product name: Vi-Cell XR) and used to determine whether or not the cells had proliferated.

From the above results, it has been confirmed that iPS cells proliferate in the cell scaffold material in which the peptide of Example 11 is used. This shows that the cyclic peptide according to the present disclosure has an excellent integrin binding property and thus has a function as the cell scaffold material.

The disclosure of JP2019-108953 filed on Jun. 11, 2019, is incorporated in the present specification by reference in its entirety.

All documents, patent applications, and technical standards described in the present specification are incorporated herein by reference, to the same extent as in the case where each of the documents, patent applications, and technical standards is specifically and individually described.

SEQUENCE LISTING

International application based on the International Patent Cooperation Treaty 19F00787W1JP20022559_24.app

What is claimed is:

1. A cyclic peptide comprising an amino acid sequence selected from the group consisting of SEQ ID NOs: 1-47.

2. A cell scaffold material comprising:
the cyclic peptide according to claim 1; and
a base material.

3. A cell separating material comprising:
the cyclic peptide according to claim 1; and
a holding material.

4. A medium comprising:
the cyclic peptide according to claim 1; and
a culture component.

5. The cyclic peptide according to claim 1, comprising an amino acid sequence selected from the group consisting of SEQ ID NOs: 3, 8, 11, 12, 14-18, 20, 22-30, 35, 38-40, and 42-47.

6. The cyclic peptide according to claim 1, comprising an amino acid sequence selected from the group consisting of SEQ ID NOs: 1-5, 7, 9, 11, and 13-47.

7. The cyclic peptide according to claim 1, comprising an amino acid sequence selected from the group consisting of SEQ ID NOs: 3, 11, 14-18, 20, 22-30, 35, 38-40, and 42-47.

* * * * *